United States Patent
Borchert et al.

(10) Patent No.: US 7,892,814 B2
(45) Date of Patent: *Feb. 22, 2011

(54) HEAT-STABLE CARBONIC ANHYDRASES AND THEIR USE

(75) Inventors: Martin Borchert, Alleroed (DK); Paria Saunders, Knightdale, NC (US)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 12/849,446

(22) Filed: Aug. 3, 2010

(65) Prior Publication Data

US 2010/0297723 A1 Nov. 25, 2010

Related U.S. Application Data

(63) Continuation of application No. 12/523,975, filed as application No. PCT/US2008/052567 on Jan. 31, 2008, now Pat. No. 7,803,575.

(60) Provisional application No. 60/887,386, filed on Jan. 31, 2007.

(30) Foreign Application Priority Data

Jan. 31, 2007 (DK) ................................ 2007 00157

(51) Int. Cl.
*C02F 3/34* (2006.01)
*C12M 1/00* (2006.01)

(52) U.S. Cl. .................... 435/262; 435/262.5; 435/266; 435/289.1

(58) Field of Classification Search ........................ None
See application file for complete search history.

(56) References Cited

U.S. PATENT DOCUMENTS

| | | | |
|---|---|---|---|
| 5,776,741 | A | 7/1998 | Pedersen et al. |
| 6,143,556 | A | 11/2000 | Trachtenberg |
| 6,524,842 | B1 | 2/2003 | Vainberg |
| 6,524,843 | B1 | 2/2003 | Blaise |
| 7,132,090 | B2 | 11/2006 | Dziedzic |
| 2004/0029257 | A1 | 2/2004 | Dutil |
| 2004/0219090 | A1 | 11/2004 | Dziedzic |
| 2004/0259231 | A1 | 12/2004 | Bhattacharya |
| 2005/0214936 | A1 | 9/2005 | Bhattacharya |
| 2006/0257990 | A1 | 11/2006 | Daigle |
| 2008/0003662 | A1 | 1/2008 | Trachtenberg |

FOREIGN PATENT DOCUMENTS

WO   WO 98/55210   12/1998

(Continued)

OTHER PUBLICATIONS

Database UniProt, "Carbonic anhydrase", XP002498957 (2004), Accession No. Q5WD44.

(Continued)

*Primary Examiner*—Nashaat T Nashed
(74) *Attorney, Agent, or Firm*—Michael W. Krenicky

(57) ABSTRACT

The present invention relates to use of heat-stable carbonic anhydrase in $CO_2$ extraction, e.g., from flue gas, natural gas or biogas. Furthermore, the invention relates to isolated polypeptides having carbonic anhydrase activity at elevated temperatures and isolated polynucleotides encoding the polypeptides. The invention also relates to nucleic acid constructs, vectors, and host cells comprising the polynucleotides.

32 Claims, 1 Drawing Sheet

FOREIGN PATENT DOCUMENTS

Figure 1:
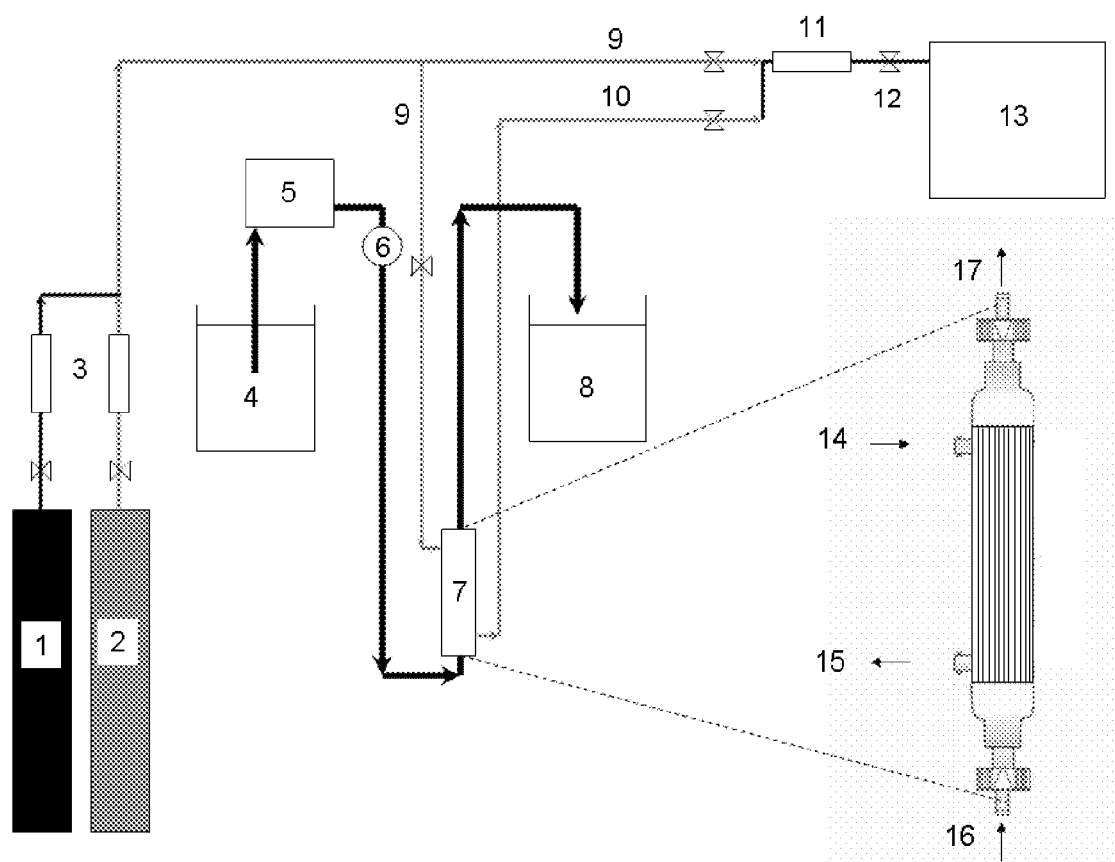

| WO | WO 2004/007058 | 1/2004 |
| WO | WO 2004/028667 | 4/2004 |
| WO | WO 2004/104160 | 12/2004 |
| WO | WO 2005/114417 | 12/2005 |
| WO | WO 2006/089423 | 8/2006 |
| WO | WO 2006/104448 | 10/2006 |
| WO | WO 2007/019859 | 2/2007 |

OTHER PUBLICATIONS

Database EMBL, "*Bacillus clausal* KSM-K16 DNA, complete genome", XP002498958 (2004), Accession No. A2006627.

Cowan et al., "CO2 capture by means of an enzyme-based reactor", Annals of the New York Academy of Sciences, vol. 984, pp. 453-469 (2003).

Bao et al., "Facilitated transport of CO2 across a liquid membrane: comparing enzyme, amine, and alkaline", Journal of Membrane Science, vol. 280, Nos. 1-2, pp. 330-334 (2006).

Smith et al., "Prokaryotic carbonic anhydrases", FEMS Microbiology Reviews Oct. 2000, vol. 24, No. 4, pp. 335-366 (2000).

Tripp et al., "Carbonic anhydrase: new insights for an ancient enzyme", The Journal of Biological Chemistry, vol. 276, No. 52, pp. 48615-48618 (2001).

Smith et al., "A plant-type (beta-class) carbonic anhydrase in the thermophilic methanoarchaeon methanobacterium thermoautotrophicum", Journal of Bacteriology, vol. 181, No. 20, pp. 6247-6253 (1999).

Alber et al., "Characterization of heterologously produced carbonic anhydrase from *Methanosarcina thermophilia*", Journal of Bacteriology, vol. 178, No. 11, pp. 3270-3274 (1996).

Alber et al., "A carbonic anhydrase from the archaeon *Methanosarcina thermophilia*", Proceedings of the National Academy of Sciences of the USA, vol. 91, No. 15, pp. 6909-6913 (1994).

Ravel et al., "Genomics at the genus scale", Trends in Microbiology, vol. 13, No. 3, pp. 95-97 (2005).

Kumar et al., "Thermostable alkaline protease from a novel marine haloalkalophilic *Bacillus clausii* isolate", World Journal of Microbiology & Biotechnology, vol. 20, No. 4, pp. 351-357 (2004).

Yavuz Elif et al., "Optimization of pulsed field gel electrophoresis (PFGE) conditions for *Thermophilic bacilli*", World Journal of Microbiology & Biotechnology, vol. 20, No. 8, pp. 871-874 (2004).

Database UniProt, Carbonic anhydrase; Accession No. Q9KFW1 (2000).

Takami et al., "Complete genome sequence of the alkaliphilic bacterium *Bacillus halodurans* and genomic sequence comparison with *Bacillus subtilis*", Nucleic Acids Research, vol. 28, No. 21, pp. 4317-4331 (2000).

Parisi et al., "Gamma carbonic anhydrases in plant mitochondria", Plant Molecular Biology, vol. 55, pp. 193-207 (2004).

Bhattacharya et al., "Co2 Hydration by Immobilized Carbonic Anhydrase", Biotechnology and Applied Biochemistry, vol. 38, pp. 111-117 (2003).

Lindskog, "Structure and Mechanism Of Carbonic Anhydrase", Pharmacology and Therapeutics, vol. 74, No. 1, pp. 1-20 (1997).

Mladenovska, "Growth Kinetics Of Thermophilic Methanosarcina Ssp. Isolated From . . . ", FEMS Microbiology Ecology, vol. 31, No. 3, pp. 225-229 (2000).

Murray et al., "Nutritional Requirements Of Methanosarcina . . . ", Applied and Environmental Microbiology, vol. 50, No. 1, pp. 49-55 (1985).

Majumdar et al., "A New Liquid Membrane Technique For Gas Separation", The American Institute of Chemical Engineers, vol. 34, No. 7, pp. 1135-1145 (1988).

Trachtenberg et al., "Carbon dioxide transport by proteic and facilitated transport membranes" Life Support and Biosphere Science, vol. 6, pp. 293-302 (1999).

Ge et al., "Enzyme-Based Facilitated Transport: Use of Vacuum Induced Sweep for Enhanced CO2 Capture", Society of Automotive Engineers, Inc. (2001).

Bao et al., "ModelingCO2-facilitated transport across a diethanolamine liquid membrane", Chemical Engineering Science, vol. 60, pp. 6868-6875 (2005).

Nielsen et al., "Phenetic diversity of alkaliphilic *Bacillus* strains: proposal for nine new species", Microbiology, vol. 141, pp. 1745-1761 (1995).

SEQUENCE LISTING

<160> NUMBER OF SEQ ID NOS: 30

<210> SEQ ID NO 1
<211> LENGTH: 717
<212> TYPE: DNA
<213> ORGANISM: Bacillus clausii

<400> SEQUENCE: 1

```
gctgctagtt tcctgtcccc gttacaagct ttgaaagcat catggtccta cgagggagag      60
acgggacctg aattttgggg agacttagac gaagcttttg ctgcgtgttc gcatggaaaa     120
gagcaatcac caatcaattt gttctttgaa agggagcaaa caccaaagtg gaattgggcc     180
ttttcatata gcgaagctgc tttttctgtt gaaaataatg gtcatacgat tcaagctaat     240
gtggaaaacg atgatgccgg tggattagaa attaatggcg aagcttatca gctcacacaa     300
ttccatttcc atactccgag tgaacatacg attgaagaag catccttccc aatggaactc     360
catcttgttc atgcaaacca tgcagggat ttagcggtgc tcggcgtttt gatggaaatt     420
ggaacagttc atgaaggcat tgaagccgtt tgggaagtca tgcctgaaga agaagggact     480
gctgaatatt ccatttctct agacccgagc ctattcctgc ctgaaagtgt aactgcttac     540
caatacgacg gttcattgac aaccctcct tgtagcgaag gggtgaaatg gacggtgctt     600
aatgacacca tttcgatttc agcaacgcaa cttcatgcat ttagggacat ctatccgcaa     660
aactatcgtc cagtccaaga gctaggcgac agagaaatcg gttttcatta tcattaa     717
```

<210> SEQ ID NO 2
<211> LENGTH: 237
<212> TYPE: PRT
<213> ORGANISM: Bacillus clausii

<400> SEQUENCE: 2

```
Ala Ser Phe Leu Ser Pro Leu Gln Ala Leu Lys Ala Ser Trp Ser Tyr
 1               5                  10                  15

Glu Gly Glu Thr Gly Pro Glu Phe Trp Gly Asp Leu Asp Glu Ala Phe
                20                  25                  30

Ala Ala Cys Ser His Gly Lys Glu Gln Ser Pro Ile Asn Leu Phe Phe
            35                  40                  45

Glu Arg Glu Gln Thr Pro Lys Trp Asn Trp Ala Phe Ser Tyr Ser Glu
        50                  55                  60

Ala Ala Phe Ser Val Glu Asn Asn Gly His Thr Ile Gln Ala Asn Val
65                  70                  75                  80

Glu Asn Asp Asp Ala Gly Gly Leu Glu Ile Asn Gly Glu Ala Tyr Gln
                85                  90                  95
```

-continued

```
Leu Thr Gln Phe His Phe His Thr Pro Ser Glu His Thr Ile Glu Glu
              100                 105                 110

Ala Ser Phe Pro Met Glu Leu His Leu Val His Ala Asn His Ala Gly
            115                 120                 125

Asp Leu Ala Val Leu Gly Val Leu Met Glu Ile Gly Thr Val His Glu
        130                 135                 140

Gly Ile Glu Ala Val Trp Glu Val Met Pro Glu Glu Gly Thr Ala
145                 150                 155                 160

Glu Tyr Ser Ile Ser Leu Asp Pro Ser Leu Phe Leu Pro Glu Ser Val
                165                 170                 175

Thr Ala Tyr Gln Tyr Asp Gly Ser Leu Thr Thr Pro Pro Cys Ser Glu
            180                 185                 190

Gly Val Lys Trp Thr Val Leu Asn Asp Thr Ile Ser Ile Ser Ala Thr
        195                 200                 205

Gln Leu His Ala Phe Arg Asp Ile Tyr Pro Gln Asn Tyr Arg Pro Val
    210                 215                 220

Gln Glu Leu Gly Asp Arg Glu Ile Gly Phe His Tyr His
225                 230                 235
```

<210> SEQ ID NO 3
<211> LENGTH: 717
<212> TYPE: DNA
<213> ORGANISM: Bacillus clausii

<400> SEQUENCE: 3

```
gctgctagtt tcctgtcccc gttacaagct ttgaaagcat catggtccta cgagggagag    60
acgggacctg aattttgggg agacttagac gaagcttttg ctgcgtgttc gcatggaaaa   120
gagcaatcac caatcaattt gttctttgaa agggagcaaa caccaaagtg gaattgggcc   180
ttttcatata gcgaagctgc tttttctgtt gaaaataatg gtcatacgat tcaagctaat   240
gtggaaaacg atgatgccgg tggattagaa attaatggcg aagcttatca gctcacacaa   300
ttccatttcc atactccgag tgaacatacg attgaaaaaa catccttccc aatggaactc   360
catcttgttc atgcaaacca tgcgggggat ttagcggtgc tcggcgtttt gatgaaatt    420
ggaacagttc atgaaggcat tgaagccgtt tgggaagtca tgcctgaaga agaagggact   480
gctgaatatt ccatttctct agacccgagc ctattcctgc ctgaaagtgt aactgcttac   540
caatacgacg gttcattgac aacccctcct tgtagcgaag ggtgaaatg acggtgcttt   600
aatgacacca tttcaatttc agcaacgcaa cttgatgcat ttagggacat ctatccgcaa   660
aactatcgtc cagtccaaga gctaggcgac agagaaatcg gttttcatta tcattaa     717
```

<210> SEQ ID NO 4
<211> LENGTH: 237
<212> TYPE: PRT
<213> ORGANISM: Bacillus clausii

<400> SEQUENCE: 4

```
Ala Ser Phe Leu Ser Pro Leu Gln Ala Leu Lys Ala Ser Trp Ser Tyr
1               5                   10                  15

Glu Gly Glu Thr Gly Pro Glu Phe Trp Gly Asp Leu Asp Glu Ala Phe
                20                  25                  30

Ala Ala Cys Ser His Gly Lys Glu Gln Ser Pro Ile Asn Leu Phe Phe
            35                  40                  45

Glu Arg Glu Gln Thr Pro Lys Trp Asn Trp Ala Phe Ser Tyr Ser Glu
50                  55                  60
```

```
Ala Ala Phe Ser Val Glu Asn Asn Gly His Thr Ile Gln Ala Asn Val
65                  70                  75                  80

Glu Asn Asp Asp Ala Gly Gly Leu Glu Ile Asn Gly Glu Ala Tyr Gln
                85                  90                  95

Leu Thr Gln Phe His Phe His Thr Pro Ser Glu His Thr Ile Glu Lys
            100                 105                 110

Thr Ser Phe Pro Met Glu Leu His Leu Val His Ala Asn His Ala Gly
        115                 120                 125

Asp Leu Ala Val Leu Gly Val Leu Met Glu Ile Gly Thr Val His Glu
    130                 135                 140

Gly Ile Glu Ala Val Trp Glu Val Met Pro Glu Glu Gly Thr Ala
145                 150                 155                 160

Glu Tyr Ser Ile Ser Leu Asp Pro Ser Leu Phe Leu Pro Glu Ser Val
                165                 170                 175

Thr Ala Tyr Gln Tyr Asp Gly Ser Leu Thr Thr Pro Pro Cys Ser Glu
            180                 185                 190

Gly Val Lys Trp Thr Val Leu Asn Asp Thr Ile Ser Ile Ser Ala Thr
        195                 200                 205

Gln Leu Asp Ala Phe Arg Asp Ile Tyr Pro Gln Asn Tyr Arg Pro Val
    210                 215                 220

Gln Glu Leu Gly Asp Arg Glu Ile Gly Phe His Tyr His
225                 230                 235
```

<210> SEQ ID NO 5
<211> LENGTH: 717
<212> TYPE: DNA
<213> ORGANISM: Bacillus clausii

<400> SEQUENCE: 5

```
gctgctagtt tcctgtcccc gctgcaagct gtgaaagcat catggtcgta tgagggggag    60
acgggacctg aattttgggg agacttagac gaagcttttg ctgcatgttc aaatggaaaa   120
gagcaatcac cagtcaattt gttttttgaa aatgggccaa caccaaagtg gaattggacc   180
tttttcttata gcgaagccgc ttttctgtt gaaaataatg ccatacgat caagcgaat    240
gtggaaaacg aggatgctgg tggattggaa attaatggcg aagcttatca gctaacacaa   300
ttccatttcc acactccgag tgaacatacg attgaagaaa catcgtttcc gatggagctc   360
catcttgttc atgcaaatcg tgcaggggat ttagcggtgc tcggcgtttt aatggaaatc   420
ggaaatggtc atgacggcat tgaagccgtt tgggaagtca tgccagaaga agaagggact   480
gctgaacatc caatttctct aaacccgagc ctattcctgc ccgaaagtgt aactgcttac   540
caatatgacg gttcattgac aacccctcct tgtagcgagg gcgtgaaatg gacagtgctg   600
aatgacacaa tctcgatttc agcagcacaa cttgatgcat ttagagacat ctatccgcaa   660
aattaccgac tgtccaaga gctaggcgac agagaaatcg gttttcatta tcattaa     717
```

<210> SEQ ID NO 6
<211> LENGTH: 237
<212> TYPE: PRT
<213> ORGANISM: Bacillus clausii

<400> SEQUENCE: 6

```
Ala Ser Phe Leu Ser Pro Leu Gln Ala Val Lys Ala Ser Trp Ser Tyr
1               5                   10                  15

Glu Gly Glu Thr Gly Pro Glu Phe Trp Gly Asp Leu Asp Glu Ala Phe
            20                  25                  30
```

-continued

```
Ala Ala Cys Ser Asn Gly Lys Glu Gln Ser Pro Val Asn Leu Phe Phe
         35                  40                  45

Glu Asn Gly Pro Thr Pro Lys Trp Asn Trp Thr Phe Ser Tyr Ser Glu
 50                  55                  60

Ala Ala Phe Ser Val Glu Asn Asn Gly His Thr Ile Gln Ala Asn Val
 65                  70                  75                  80

Glu Asn Glu Asp Ala Gly Gly Leu Glu Ile Asn Gly Glu Ala Tyr Gln
                 85                  90                  95

Leu Thr Gln Phe His Phe His Thr Pro Ser Glu His Thr Ile Glu Glu
                100                 105                 110

Thr Ser Phe Pro Met Glu Leu His Leu Val His Ala Asn Arg Ala Gly
                115                 120                 125

Asp Leu Ala Val Leu Gly Val Leu Met Glu Ile Gly Asn Gly His Asp
130                 135                 140

Gly Ile Glu Ala Val Trp Glu Val Met Pro Glu Glu Gly Thr Ala
145                 150                 155                 160

Glu His Pro Ile Ser Leu Asn Pro Ser Leu Phe Leu Pro Glu Ser Val
                165                 170                 175

Thr Ala Tyr Gln Tyr Asp Gly Ser Leu Thr Thr Pro Pro Cys Ser Glu
                180                 185                 190

Gly Val Lys Trp Thr Val Leu Asn Asp Thr Ile Ser Ile Ser Ala Ala
                195                 200                 205

Gln Leu Asp Ala Phe Arg Asp Ile Tyr Pro Gln Asn Tyr Arg Pro Val
210                 215                 220

Gln Glu Leu Gly Asp Arg Glu Ile Gly Phe His Tyr His
225                 230                 235
```

```
<210> SEQ ID NO 7
<211> LENGTH: 717
<212> TYPE: DNA
<213> ORGANISM: Bacillus clausii

<400> SEQUENCE: 7
gctgctagtt tcctgtcacc gttacaagct ttgaaagcat catggtcgta tgaggggggac    60 acgggacctg aattttgggg agacttagac gaagcgtttg ctgcgtgttc gaatggaaaa   120
gagcaatcac caatcaattt gttttatgat cgtgagcaaa caccgaagtg gaattgggcc   180
ttttcatata gcgaagctgc ttttttctgtt gaaaataatg gcatacgat caagctaat    240 gtggaaaatg aggatgccgg tggtttagaa attaatggcg aagcttatca gctgacacaa   300
ttccatttcc atactccgag tgaacatacg attgaagaaa catccttctcc gatggagctt   360 catcttgttc atgcaaatca tgcagggggat ttagcggtgc tcggcgtttt gatgaaatt    420 ggcaatgatc atgaaggcat tgaagccgtt tgggaagtca tgcccgaaga gaagggact    480 gctgagtatt ccatttctat agacccgagc ctattcctgc ctgaaagtgt gactgcttac   540
caatacgacg gttcattgac aaccccctcct tgtagcgaag gcgtgaaatg gacgggtgctt   600 aatgacacca tttcgatttc agcaacgcaa cttgatgcat ttagggccat ctatccacaa   660
aactaccgtc cagtccaaga gctaggcgac agagaaatcg gttttcatta tcattaa       717

<210> SEQ ID NO 8
<211> LENGTH: 237
<212> TYPE: PRT
<213> ORGANISM: Bacillus clausii

<400> SEQUENCE: 8
```

```
Ala Ser Phe Leu Ser Pro Leu Gln Ala Leu Lys Ala Ser Trp Ser Tyr
1               5                   10                  15
Glu Gly Asp Thr Gly Pro Glu Phe Trp Gly Asp Leu Asp Glu Ala Phe
            20                  25                  30
Ala Ala Cys Ser Asn Gly Lys Glu Gln Ser Pro Ile Asn Leu Phe Tyr
        35                  40                  45
Asp Arg Glu Gln Thr Pro Lys Trp Asn Trp Ala Phe Ser Tyr Ser Glu
50                  55                  60
Ala Ala Phe Ser Val Glu Asn Asn Gly His Thr Ile Gln Ala Asn Val
65                  70                  75                  80
Glu Asn Glu Asp Ala Gly Gly Leu Glu Ile Asn Gly Glu Ala Tyr Gln
                85                  90                  95
Leu Thr Gln Phe His Phe His Thr Pro Ser Glu His Thr Ile Glu Glu
                100                 105                 110
Thr Ser Phe Pro Met Glu Leu His Leu Val His Ala Asn His Ala Gly
            115                 120                 125
Asp Leu Ala Val Leu Gly Val Leu Met Glu Ile Gly Asn Asp His Glu
        130                 135                 140
Gly Ile Glu Ala Val Trp Glu Val Met Pro Glu Glu Gly Thr Ala
145                 150                 155                 160
Glu Tyr Ser Ile Ser Ile Asp Pro Ser Leu Phe Leu Pro Glu Ser Val
                165                 170                 175
Thr Ala Tyr Gln Tyr Asp Gly Ser Leu Thr Thr Pro Pro Cys Ser Glu
            180                 185                 190
Gly Val Lys Trp Thr Val Leu Asn Asp Thr Ile Ser Ile Ser Ala Thr
        195                 200                 205
Gln Leu Asp Ala Phe Arg Ala Ile Tyr Pro Gln Asn Tyr Arg Pro Val
210                 215                 220
Gln Glu Leu Gly Asp Arg Glu Ile Gly Phe His Tyr His
225                 230                 235

<210> SEQ ID NO 9
<211> LENGTH: 717
<212> TYPE: DNA
<213> ORGANISM: Bacillus clausii

<400> SEQUENCE: 9
gctgctagtt tcctgtcccc gctgcaagct gtgaaagcat catggtcgta tgagggggag      60
acgggacctg aatttggggg agacttagac gaagcttttg ctgcgtgttc aaatggaaaa     120
gagcaatcac cagtcaattt gttttttgaa atgggccgga caccaaagtg gaattggacc     180
ttttcttata gcaagccgc ttttctgtt gaaataatg ccatacgat tcaagcgaat         240 gtggaaaacg atgatgctgg tggattggaa attaatggtg aagcttatca gctaacacaa     300
ttccatttcc acactccgag tgaacataca attgaagaaa cattgttttcc gatggagctc    360 catcttgttc atgccaatca tgcaggggat ttagcggtac tcggtgtttt gatggaaatc     420
ggaaatggtc atgagggcat tgaaaccgtt tgggaaatca tgccggaaga agaagggact     480
gctgaacatc aatttctct aaacccgagc ctattcctgc cgaaaatgt aactgcttac      540 caatatgacg gttcattgac aacccctcct tgtagcgagg gcgtgaaatg gacagtgctg     600
aatgacacaa tctcgatttc agcagcacaa cttgatgcgt ttagcgacat ctatccgcaa     660
aattaccgac tgtccaaga gctaggcgac agagaaatcg gttttcatta tcattaa        717

<210> SEQ ID NO 10
```

<211> LENGTH: 237
<212> TYPE: PRT
<213> ORGANISM: Bacillus clausii

<400> SEQUENCE: 10

| Ala | Ser | Phe | Leu | Ser | Pro | Leu | Gln | Ala | Val | Lys | Ala | Ser | Trp | Ser | Tyr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Glu Gly Glu Thr Gly Pro Glu Phe Trp Gly Asp Leu Asp Glu Ala Phe
                20                  25                  30

Ala Ala Cys Ser Asn Gly Lys Glu Gln Ser Pro Val Asn Leu Phe Phe
            35                  40                  45

Glu Asn Gly Pro Thr Pro Lys Trp Asn Trp Thr Phe Ser Tyr Ser Glu
        50                  55                  60

Ala Ala Phe Ser Val Glu Asn Asn Gly His Thr Ile Gln Ala Asn Val
65                  70                  75                  80

Glu Asn Asp Asp Ala Gly Gly Leu Glu Ile Asn Gly Glu Ala Tyr Gln
                85                  90                  95

Leu Thr Gln Phe His Phe His Thr Pro Ser Glu His Thr Ile Glu Glu
            100                 105                 110

Thr Leu Phe Pro Met Glu Leu His Leu Val His Ala Asn His Ala Gly
        115                 120                 125

Asp Leu Ala Val Leu Gly Val Leu Met Glu Ile Gly Asn Gly His Gly
130                 135                 140

Gly Ile Glu Thr Val Trp Glu Ile Met Pro Glu Glu Gly Thr Ala
145                 150                 155                 160

Glu His Pro Ile Ser Leu Asn Pro Ser Leu Phe Leu Pro Glu Asn Val
            165                 170                 175

Thr Ala Tyr Gln Tyr Asp Gly Ser Leu Thr Thr Pro Pro Cys Ser Glu
        180                 185                 190

Gly Val Lys Trp Thr Val Leu Asn Asp Thr Ile Ser Ile Ser Ala Ala
    195                 200                 205

Gln Leu Asp Ala Phe Ser Asp Ile Tyr Pro Gln Asn Tyr Arg Pro Val
210                 215                 220

Gln Glu Leu Gly Asp Arg Glu Ile Gly Phe His Tyr His
225                 230                 235

<210> SEQ ID NO 11
<211> LENGTH: 717
<212> TYPE: DNA
<213> ORGANISM: Bacillus clausii

<400> SEQUENCE: 11

```
gctgctagtt tcctgtcacc gttacaagct tgaaagcat catggtcgta tgaggggggac        60
acgggacctg aattttgggg agacttagac gaagcgtttg ctgcgtgttc gaatggaaaa       120
gagcaatcac caatcaattt gttttatgat cgtgagcaaa caccgaagtg gaattgggcc       180
ttttcatata gcgaagctgc ttttcctgtt gaaaataatg gcatacgat tcaagctaat       240
gtggaaaatg aggatgccgg tggtttagaa attaatggcg aagcttatca gctgacacaa       300
ttccatttcc atactccgag tgaacatacg attgaagaaa catcctttcc gatggagctt       360
catcttgttc atgcaaatca tgcaggggat ttagcggtgc tcggagtttt gatgaaatt       420
ggcaatgatc atgaaggcat tgaagccgtt tgggaagtca tgcccgaaga agaagggact       480
gctgagtatt ccattctat agaccccgagc ctattcctgc ctgaaagtgt gactgcttac       540
caatacgacg gttcattgac aacccctcct tgtagcgaag cgtgaaatg gacggtgctt       600
```
aatgacacca tttcgatttc agcaacgcaa ctcgatgcat ttagggacat ctatccacaa    660
aactaccgtc cagtccaaga gctaggcgac agagaaatcg gttttcatta tcattaa      717

<210> SEQ ID NO 12
<211> LENGTH: 237
<212> TYPE: PRT
<213> ORGANISM: Bacillus clausii

<400> SEQUENCE: 12

```
Ala Ser Phe Leu Ser Pro Leu Gln Ala Leu Lys Ala Ser Trp Ser Tyr
1               5                   10                  15

Glu Gly Asp Thr Gly Pro Glu Phe Trp Gly Asp Leu Asp Glu Ala Phe
            20                  25                  30

Ala Ala Cys Ser Asn Gly Lys Glu Gln Ser Pro Ile Asn Leu Phe Tyr
        35                  40                  45

Asp Arg Glu Gln Thr Pro Lys Trp Asn Trp Ala Phe Ser Tyr Ser Glu
    50                  55                  60

Ala Ala Phe Ser Val Glu Asn Asn Gly His Thr Ile Gln Ala Asn Val
65                  70                  75                  80

Glu Asn Glu Asp Ala Gly Gly Leu Glu Ile Asn Gly Glu Ala Tyr Gln
                85                  90                  95

Leu Thr Gln Phe His Phe His Thr Pro Ser Glu His Thr Ile Glu Glu
            100                 105                 110

Thr Ser Phe Pro Met Glu Leu His Leu Val His Ala Asn His Ala Gly
        115                 120                 125

Asp Leu Ala Val Leu Gly Val Leu Met Glu Ile Gly Asn Asp His Glu
    130                 135                 140

Gly Ile Glu Ala Val Trp Glu Val Met Pro Glu Glu Glu Gly Thr Ala
145                 150                 155                 160

Glu Tyr Ser Ile Ser Ile Asp Pro Ser Leu Phe Leu Pro Glu Ser Val
                165                 170                 175

Thr Ala Tyr Gln Tyr Asp Gly Ser Leu Thr Thr Pro Pro Cys Ser Glu
            180                 185                 190

Gly Val Lys Trp Thr Val Leu Asn Asp Thr Ile Ser Ile Ser Ala Thr
        195                 200                 205

Gln Leu Asp Ala Phe Arg Asp Ile Tyr Pro Gln Asn Tyr Arg Pro Val
    210                 215                 220

Gln Glu Leu Gly Asp Arg Glu Ile Gly Phe His Tyr His
225                 230                 235
```

<210> SEQ ID NO 13
<211> LENGTH: 717
<212> TYPE: DNA
<213> ORGANISM: Bacillus clausii

<400> SEQUENCE: 13
gctgctagtt tcctgtcacc gttacaagct ttgaaagcat catggtcgta tgaggggag    60 acgggacctg aatttggggg agacttagac gaagcgtttg ctgcgtgttc gaatggaaaa   120
gagcaatcac caatcaattt gttttatgat cgtgagcaaa catcaaagtg gaattgggcc   180
ttttcatata gcgaagctgc ttttctgtt gaaataatg gcatacgat tcaagctaat      240 gtggaaaatg aggatgccgg tggtttagaa attaatggcg aagcttatca gctgatacaa   300
ttccatttcc atactccgag tgaacatacg attgaagaaa catcctttcc gatggagctt   360
catctagttc atgcaaatca tgcaggggat ttagcggtgc tcggcgtttt gatggaaatg   420

```
ggcaatgatc atgaaggcat tgaagccgtt tgggaagtca tgcccgaaga agaagggact    480
gctgcgtatt ccatttctct agacccgaac ctattcctgc cggaaagtgt gactgcttac    540
caatacgacg gttcattgac aaccccctcct tgtagcgaag gcgtaaaatg acagtgctt    600 aacgacacca tttcgatttc agaaacgcaa cttgatgcat ttagggacat ctatccacaa    660
aactaccgtc ctgtccaaga gctaggcgac agagaaatcg gttttcatta tcattaa      717
```

<210> SEQ ID NO 14
<211> LENGTH: 237
<212> TYPE: PRT
<213> ORGANISM: Bacillus clausii

<400> SEQUENCE: 14

```
Ala Ser Phe Leu Ser Pro Leu Gln Ala Leu Lys Ala Ser Trp Ser Tyr
1               5                   10                  15

Glu Gly Glu Thr Gly Pro Glu Phe Trp Gly Asp Leu Asp Glu Ala Phe
            20                  25                  30

Ala Ala Cys Ser Asn Gly Lys Glu Gln Ser Pro Ile Asn Leu Phe Tyr
        35                  40                  45

Asp Arg Glu Gln Thr Ser Lys Trp Asn Trp Ala Phe Ser Tyr Ser Glu
    50                  55                  60

Ala Ala Phe Ser Val Glu Asn Asn Gly His Thr Ile Gln Ala Asn Val
65                  70                  75                  80

Glu Asn Glu Asp Ala Gly Gly Leu Glu Ile Asn Gly Glu Ala Tyr Gln
                85                  90                  95

Leu Ile Gln Phe His Phe His Thr Pro Ser Glu His Thr Ile Glu Glu
            100                 105                 110

Thr Ser Phe Pro Met Glu Leu His Leu Val His Ala Asn His Ala Gly
        115                 120                 125

Asp Leu Ala Val Leu Gly Val Leu Met Glu Met Gly Asn Asp His Glu
    130                 135                 140

Gly Ile Glu Ala Val Trp Glu Val Met Pro Glu Glu Gly Thr Ala
145                 150                 155                 160

Ala Tyr Ser Ile Ser Leu Asp Pro Asn Leu Phe Leu Pro Glu Ser Val
                165                 170                 175

Thr Ala Tyr Gln Tyr Asp Gly Ser Leu Thr Thr Pro Pro Cys Ser Glu
            180                 185                 190

Gly Val Lys Trp Thr Val Leu Asn Asp Thr Ile Ser Ile Ser Glu Thr
        195                 200                 205

Gln Leu Asp Ala Phe Arg Asp Ile Tyr Pro Gln Asn Tyr Arg Pro Val
    210                 215                 220

Gln Glu Leu Gly Asp Arg Glu Ile Gly Phe His Tyr His
225                 230                 235
```

<210> SEQ ID NO 15
<211> LENGTH: 753
<212> TYPE: DNA
<213> ORGANISM: Bacillus halodurans

<400> SEQUENCE: 15

```
ccttccacag aaccagtcga tgagccgagc gagacacatg aggaaacgag cggtggcgca    60
cacgaggttc attggtctta cactggagac actggtccag agcattgggc agagttggat   120
tcggaatatg gtgcttgcgc tcaaggagaa gagcagtcac cgatcaactt agacaaagcg   180
gaggccgttg ataccgatac cgaaatccaa gttcattatg agccgagcgc gtttacgatt   240
```

-continued

```
aaaaataatg gtcacacgat tcaagcagag actacctcag atgggaacac gattgaaatc    300
gatggaaaag aatacacact cgttcaattc cacttccata ttccttccga gcatgaaatg    360
gaaggaaaga atttagatat ggagctacat tttgtccata aaaatgaaaa cgacgagctc    420
gccgtactcg gggtcttaat gaaggccggc gaagagaacg aagagctagc gaagctatgg    480
tcgaagctac cagcagaaga aacagaagaa aatatttcgt tagatgagtc aattgatttg    540
aacgcgctct taccagaaag caagaaggga ttccattaca acggttcctt aacgacgcct    600
ccttgctcag aagggtaaa gtggaccgtg ctatctgaac cgattactgt ttcacaagag    660
caaatcgacg cgtttgctga tcttccca gacaatcacc gaccagtcca accttggaac    720
gaccgtgatg tctatgacgt gatcactgaa tag                                753
```

<210> SEQ ID NO 16
<211> LENGTH: 250
<212> TYPE: PRT
<213> ORGANISM: Bacillus halodurans

<400> SEQUENCE: 16

```
Pro Ser Thr Glu Pro Val Asp Glu Pro Ser Glu Thr His Glu Thr
1               5                   10                  15

Ser Gly Gly Ala His Glu Val His Trp Ser Tyr Thr Gly Asp Thr Gly
            20                  25                  30

Pro Glu His Trp Ala Glu Leu Asp Ser Glu Tyr Gly Ala Cys Ala Gln
        35                  40                  45

Gly Glu Glu Gln Ser Pro Ile Asn Leu Asp Lys Ala Glu Ala Val Asp
    50                  55                  60

Thr Asp Thr Glu Ile Gln Val His Tyr Glu Pro Ser Ala Phe Thr Ile
65                  70                  75                  80

Lys Asn Asn Gly His Thr Ile Gln Ala Glu Thr Thr Ser Asp Gly Asn
                85                  90                  95

Thr Ile Glu Ile Asp Gly Lys Glu Tyr Thr Leu Val Gln Phe His Phe
            100                 105                 110

His Ile Pro Ser Glu His Glu Met Glu Gly Lys Asn Leu Asp Met Glu
        115                 120                 125

Leu His Phe Val His Lys Asn Glu Asn Asp Glu Leu Ala Val Leu Gly
    130                 135                 140

Val Leu Met Lys Ala Gly Glu Glu Asn Glu Glu Leu Ala Lys Leu Trp
145                 150                 155                 160

Ser Lys Leu Pro Ala Glu Glu Thr Glu Glu Asn Ile Ser Leu Asp Glu
                165                 170                 175

Ser Ile Asp Leu Asn Ala Leu Leu Pro Glu Ser Lys Glu Gly Phe His
            180                 185                 190

Tyr Asn Gly Ser Leu Thr Thr Pro Pro Cys Ser Glu Gly Val Lys Trp
        195                 200                 205

Thr Val Leu Ser Glu Pro Ile Thr Val Ser Gln Glu Gln Ile Asp Ala
    210                 215                 220

Phe Ala Glu Ile Phe Pro Asp Asn His Arg Pro Val Gln Pro Trp Asn
225                 230                 235                 240

Asp Arg Asp Val Tyr Asp Val Ile Thr Glu
                245                 250
```

<210> SEQ ID NO 17
<211> LENGTH: 12
<212> TYPE: PRT
<213> ORGANISM: Artificial Sequence
<220> FEATURE:
<223> OTHER INFORMATION: alignment example

<400> SEQUENCE: 17

Ala Cys Met Ser His Thr Trp Gly Glu Arg Asn Leu
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Alignment example

<400> SEQUENCE: 18

His Gly Trp Gly Glu Asp Ala Asn Leu Ala Met Asn Pro Ser
1               5                   10

<210> SEQ ID NO 19
<211> LENGTH: 24
<212> TYPE: DNA
<213> ORGANISM: Artificial Sequence
<220> FEATURE:
<223> OTHER INFORMATION: primer

<400> SEQUENCE: 19
gcttctgctg ctagtttcct gtca                                          24

<210> SEQ ID NO 20
<211> LENGTH: 26
<212> TYPE: DNA
<213> ORGANISM: Artificial Sequence
<220> FEATURE:
<223> OTHER INFORMATION: Primer

<400> SEQUENCE: 20
ataatgaaaa ccgatttctc tgtcgc                                        26

<210> SEQ ID NO 21
<211> LENGTH: 42
<212> TYPE: DNA
<213> ORGANISM: Artificial Sequence
<220> FEATURE:
<223> OTHER INFORMATION: Primer

<400> SEQUENCE: 21
cttgctgcct cattctgcag ccgcgttgaa agcatcatgg tc                      42

<210> SEQ ID NO 22
<211> LENGTH: 44
<212> TYPE: DNA
<213> ORGANISM: Artificial Sequence
<220> FEATURE:
<223> OTHER INFORMATION: Primer

<400> SEQUENCE: 22
tccgatcccc ttttccattc tactttaatg ataatgaaaa ccga                    44

<210> SEQ ID NO 23
<211> LENGTH: 42
<212> TYPE: DNA
<213> ORGANISM: Artificial Sequence
<220> FEATURE:
<223> OTHER INFORMATION: Primer

<400> SEQUENCE: 23
ctgcctcatt ctgcagccgc gccttccaca gaaccagtcg at                42

<210> SEQ ID NO 24
<211> LENGTH: 44
<212> TYPE: DNA
<213> ORGANISM: Artificial Sequence
<220> FEATURE:
<223> OTHER INFORMATION: Primer

<400> SEQUENCE: 24
tccgatcccc ttttccattc tactctattc agtgatcacg tcat              44

<210> SEQ ID NO 25
<211> LENGTH: 10
<212> TYPE: PRT
<213> ORGANISM: Artificial Sequence
<220> FEATURE:
<223> OTHER INFORMATION: recombinant protein

<400> SEQUENCE: 25

Leu Lys Ala Ser Trp Ser Tyr Glu Gly Glu
1               5                   10

<210> SEQ ID NO 26
<211> LENGTH: 10
<212> TYPE: PRT
<213> ORGANISM: Artificial Sequence
<220> FEATURE:
<223> OTHER INFORMATION: recombinant protein

<400> SEQUENCE: 26

Leu Lys Ala Ser Trp Ser Tyr Glu Gly Asp
1               5                   10

<210> SEQ ID NO 27
<211> LENGTH: 10
<212> TYPE: PRT
<213> ORGANISM: Artificial Sequence
<220> FEATURE:
<223> OTHER INFORMATION: recombinant protein

<400> SEQUENCE: 27

Leu Lys Ala Ser Trp Ser Tyr Glu Gly Glu
1               5                   10

<210> SEQ ID NO 28
<211> LENGTH: 10
<212> TYPE: PRT
<213> ORGANISM: Artificial Sequence
<220> FEATURE:
<223> OTHER INFORMATION: recombinant protein

<400> SEQUENCE: 28

Leu Lys Ala Ser Trp Ser Tyr Glu Gly Asp
1               5                   10

<210> SEQ ID NO 29
<211> LENGTH: 8
<212> TYPE: PRT
<213> ORGANISM: Artificial Sequence
<220> FEATURE:
<223> OTHER INFORMATION: recombinant protein

<400> SEQUENCE: 29

Leu Lys Ala Ser Trp Ser Tyr Glu
1               5

```
<210> SEQ ID NO 30
<211> LENGTH: 10
<212> TYPE: PRT
<213> ORGANISM: Artificial Sequence
<220> FEATURE:
<223> OTHER INFORMATION: recombinant protein

<400> SEQUENCE: 30

Gly Gly Ala His Glu Val His Trp Ser Tyr
1               5                   10
```

HEAT-STABLE CARBONIC ANHYDRASES AND THEIR USE

CROSS-REFERENCE TO RELATED APPLICATIONS

This application is a continuation of U.S. application Ser. No. 12/523,975 (now allowed) filed Jul. 21, 2009 which is a 35 U.S.C. 371 national application of PCT/US2008/052567 filed Jan. 31, 2008, which claims priority or the benefit under 35 U.S.C. 119 of Danish application no. PA 2007 00157 filed Jan. 31, 2007 and U.S. provisional application No. 60/887,386 filed Jan. 31, 2007, the contents of which are fully incorporated herein by reference.

FIELD OF THE INVENTION

The present invention relates to use of heat-stable carbonic anhydrase at elevated temperature in $CO_2$ extraction, e.g., from flue gasses, biogas or natural gas. The invention also relates to bioreactors for extracting carbon dioxide. Furthermore, the invention relates to isolated polypeptides having carbonic anhydrase activity at elevated temperatures and isolated polynucleotides encoding the polypeptides, as well as formulation of the polypeptide. The invention also relates to nucleic acid constructs, vectors, and host cells comprising the polynucleotides.

BACKGROUND OF THE INVENTION

Carbonic anhydrases (CA, EC 4.2.1.1, also termed carbonate dehydratases) catalyze the inter-conversion between carbon dioxide and bicarbonate $[CO_2+H_2O \leftrightarrows HCO_3^-+H^+]$. The enzyme was discovered in bovine blood in 1933 (Meldrum and Roughton, 1933, *J. Physiol.* 80: 113-142) and has since been found widely distributed in nature in all domains of life. These enzymes are categorized in three distinct classes called the alpha-, beta- and gamma-class, and potentially a fourth class, the delta-class. These classes evolved from independent origins (Bacteria, Archaea, Eukarya) and have no significant sequence or structural identity, except for single zinc atom at the catalytic site (for review see Tripp et al., 2001, *J. Biol. Chem.* 276: 48615-48618). For alpha-CAs more than 11 isozymes have been identified in mammals. Alpha-carbonic anhydrases are abundant in all mammalian tissues where they facilitate the removal of $CO_2$. Beta-CAs are ubiquitous in algae and plants where they provide for $CO_2$ uptake and fixation for photosynthesis. The gamma-class of CAs is believed to have evolved first. The only gamma-CA that has been isolated and characterized so far is from the Archaeon *Methanosarcina thermophila* strain TM-1 (Alber and Ferry, 1994, *Proc. Natl. Acad. Sci. USA* 91: 6909-6913), however many gamma-type carbonic anhydrases have been proposed by Parisi et al., 2004, *Plant Mol. Biol.* 55: 193-207. In prokaryotes genes encoding all three CA classes have been identified, with the beta- and gamma-class predominating. Many prokaryotes contain carbonic anhydrase genes from more than one class or several genes of the same class (for review see Smith and Ferry, 2000, *FEMS Microbiol. Rev.* 24: 335-366; Tripp et al., 2001. *J. Biol. Chem.* 276: 48615-48618).

Carbon dioxide ($CO_2$) emissions are a major contributor to the phenomenon of global warming. $CO_2$ is a by-product of combustion and it creates operational, economic, and environmental problems. $CO_2$ emissions may be controlled by capturing $CO_2$ gas before emitted into the atmosphere. There are several chemical approaches to control the $CO_2$ emissions. However, many of these approaches have draw backs such as high energy consumption, slow processes, and use of ecological questionable or toxic compounds.

An enzyme based solution using the capability of carbonic anhydrase to catalyse the conversion of $CO_2$ to bicarbonate at a very high rate (turnover is up to $10^5$ molecules of $CO_2$ per second), takes care of the speed and environmental issues in relation to $CO_2$ capture. Technical solutions for extracting $CO_2$ from gases, such as combustion gases or respiration gases, using carbonic anhydrases have been described in WO 2006/089423, U.S. Pat. No. 6,524,842, WO 2004/007058, WO 2004/028667, US 2004/0029257, U.S. Pat. No. 7,132,090, WO 2005/114417, U.S. Pat. No. 6,143,556, WO 2004/104160, US 2005/214936. Generally, these techniques operate by bringing a soluble or immobilized carbonic anhydrase into contact with $CO_2$ which either may be in a gas phase or a liquid phase. The carbonic anhydrase catalyses the conversion of $CO_2$ into bicarbonate and/or carbonate ions. The ions may either be utilized to facilitate growth of algae or other microorganisms, to induce a pH change in a surrounding medium or supply buffering capacity, to provide bicarbonate/carbonate as an active agent for subsequent chemical processes, or precipitated as a carbonate salt, or converted back into pure $CO_2$, which can then be used (for example in enhanced oil recovery, for production of urea, for food and beverage processing, or to supply $CO_2$ to greenhouses), released (for example from a contained life support environment such as a submarine or spacecraft), compressed (for example for transportation through pipelines), or stored under compression (such as in geological or deep oceanic formations).

Mammalian, plant and prokaryotic carbonic anhydrases (alpha- and beta-class CAs) generally function at physiological temperatures (37° C.) or lower temperatures. The temperature of combustion gasses or the liquids into which they are dissolved may, however, easily exceed the temperature optimum for the carbonic anhydrase used to capture the $CO_2$. Thus, one of the drawbacks of using enzyme based solutions is that extensive cooling may be need prior to contacting the $CO_2$-containing gas/liquid with the carbonic anhydrase, and cooling is an energy consuming process.

SUMMARY OF THE INVENTION

One aspect of the present invention, is the use of heat-stable carbonic anhydrase of bacterial or archaeal or fungal origin, but excluding gamma-class carbonic anhydrase from *Methanosarcina thermophila* strain TM-1 (DSM 1825), for extraction of carbon dioxide from a carbon dioxide-containing medium. The heat-stable carbonic anhydrase useful in the present invention maintain activity at temperatures above 45° C. for at least 15 minutes. The heat-stable carbonic anhydrases are in particular used in a bioreactor capable of extracting $CO_2$ emitted from combustion, or from raw natural gas or a syngas or a biogas. The heat stability is also useful when exposing carbonic anhydrase to environments where the temperature can exceed 45° C. during use, or during idle periods, for example storage in a hot warehouse.

In another aspect, the present invention provides an isolated polypeptide having carbonic anhydrase activity at elevated temperatures, selected from the group consisting of:

a) a polypeptide having an amino acid sequence which has at least 94% identity with the amino acid sequence of SEQ ID NO: 2 or SEQ ID NO: 4, or at least 91% identity with the amino acid sequence of SEQ ID NO: 6, or at least 96% identity with the amino acid sequence of SEQ ID NO: 8, or at least 87% identity with the amino acid sequence of SEQ ID NO: 10, or at least 97% identity with the amino acid sequence of SEQ ID NO: 12;

b) a polypeptide encoded by a nucleic acid sequence which hybridizes under medium stringency conditions with:
i) a polynucleotide sequence encoding a mature polypeptide selected from the group consisting of SEQ ID NO: 2, SEQ ID NO: 4, SEQ ID NO: 6, SEQ ID NO: 8, SEQ ID NO: 10 and SEQ ID NO: 12,
ii) a polynucleotide sequence selected from the group consisting of regions of SEQ ID NO: 1, SEQ ID NO:3, SEQ ID NO: 5, SEQ ID NO: 7, SEQ ID NO: 9 and SEQ ID NO: 11 encoding a mature enzyme,
iii) the cDNA sequence contained in a polynucleotide sequence selected from the group consisting of regions of SEQ ID NO: 1, SEQ ID NO: 3, SEQ ID NO: 5, SEQ ID NO: 7, SEQ ID NO: 9 and SEQ ID NO: 11 encoding a mature enzyme,
iv) a subsequence of (i), (ii) or (iii) of at least 100 contiguous nucleotides, or
v) a complementary strand of (i), (ii), (iii) or (iv); and c) a fragment of (a) or (b) having carbonic anhydrase activity.

In a further aspect, the invention provides a composition comprising a polypeptide of the invention and a method for preparing such a composition comprising admixing the polypeptide of the invention with an excipient.

In further aspects, the invention provides an isolated polynucleotide having a nucleotide sequence which encodes for a polypeptide of the invention and a nucleic acid construct comprising such a polynucleotide as well as a recombinant vector or recombinant host cell comprising such a nucleic acid construct.

In a further aspect, the present invention provides a method for producing the polypeptide of the present invention by cultivating a strain, which in its wild-type form is capable of producing the polypeptide, or by cultivation of a recombinant host cell comprising a recombinant expression vector coding for a polypeptide of the present invention under conditions conducive for production of the polypeptide and recovering the polypeptide.

In a further aspect, the present invention provides a bioreactor suitable for extracting carbon dioxide.

DRAWINGS

FIG. 1 is a schematic presentation of a hollow fiber contained liquid membrane bioreactor. The numbers represent the following features: 1. Carbon Dioxide ($CO_2$) tank; 2. Nitrogen ($N_2$) or Methane ($CH_4$) tank; 3. Mass flow controllers (MFC); 4. Membrane liquid reservoir; 5. Liquid pump; 6. Pressure gauge; 7. Hollow fiber membrane bioreactor (module); 8. Waste; 9. Feed gas; 10. Scrubbed gas; 11. Mass flow meter (MFM); 12 Gas sampling valve; 13. Gas chromatograph; 14. Feed gas in; 15. Scrubbed gas out; 16. Liquid in; 17. Liquid out.

DETAILED DESCRIPTION OF THE INVENTION

One aspect of the present invention concerns the use of heat-stable carbonic anhydrases for the extraction of $CO_2$ from $CO_2$-containing media, such as a gas, a liquid or multiphase mixture. The present invention is in particular useful where the temperature of the $CO_2$-containing medium is above the temperature optimum for commercially available carbonic anhydrases, such as CA-I or CA-II isolated from human or bovine erythrocytes.

A further aspect of the invention is to provide heat-stable carbonic anhydrases suitable for extracting $CO_2$ from gas phases or solutions with temperatures above the temperature optimum for commercially available carbonic anhydrases, such as CA-I or CA-II isolated from human or bovine erythrocytes. Heat-stable carbonic anhydrases of the present invention are preferably of bacterial or archaeal or fungal origin and may be of any of the distinct CA classes; alpha, beta, gamma or delta, except for the gamma-class carbonic anhydrase from *Methanosarcina thermophila* TM-1 (DSM 1825). In a preferred embodiment the carbonic anhydrases belong to the alpha- or beta-class, and more preferred they belong to the alpha-class.

Definitions

The term "archaeal origin" includes molecules such as polypeptides, nucleic acids, DNA and RNA derived from archaea. It is also intended to include modified or mutated molecules where the parent molecule originally was derived from archaea. The origin of the modified or mutated molecule should still be recognizable, preferably polypeptide and nucleic acid sequences are at least 60% identical to the parent molecule, more preferably it is at least 65%, 70%, 75%, 80%, 85%, 90%, 95%, 96%, 97%, 98% or 99% identical to the parent molecule.

The term "bacterial origin" includes molecules such as polypeptides, nucleic acids, DNA and RNA derived from bacteria. It is also intended to include modified or mutated molecules where the parent molecule originally was derived from bacteria. The origin of the modified or mutated molecule should still be recognizable, preferably polypeptide and nucleic acid sequences are at least 60% identical to the parent molecule, more preferably it is at least 65%, 70%, 75%, 80%, 85%, 90%, 95%, 96%, 97%, 98% or 99% identical to the parent molecule.

The term "carbonic anhydrase activity" or "CA activity" is defined herein as an EC 4.2.1.1 activity which catalyzes the inter-conversion between carbon dioxide and bicarbonate $[CO_2+H_2O \leftrightarrows HCO_3^-+H^+]$. For purposes of the present invention, CA activity is determined according to the procedure described in Example 3 or 4. One unit of CA activity is defined after Wilbur [1 $U=(1/t_c)-(1/t_u) \times 1000$] where U is units and $t_c$ and $t_o$ represent the time in seconds for the catalyzed and uncatalyzed reaction, respectively (Wilbur, 1948, *J. Biol. Chem.* 176: 147-154). The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the CA activity of the polypeptide consisting of the amino acid sequence of SEQ ID NO: 14.

The term "$CO_2$-containing medium" is used to describe any material which may contain at least 0.001% $CO_2$, preferably at least 0.01%, more preferably at least 0.1%, more preferably at least 1%, more preferably at least 5%, most preferably 10%, even more preferred at least 20%, and even most preferably at least 50% $CO_2$. Preferably the $CO_2$-containing medium has a temperature between 45° C. and 100° C., more preferably between 45° C. and 80° C., even more preferably between 45° C. and 60° C., and most preferably between 45° C. and 55° C. $CO_2$-containing media are in particular gaseous phases, liquids or multiphase mixtures, but may also be solid. A $CO_2$-containing gaseous phase is for example raw natural gas obtainable from oil wells, gas wells, and condensate wells, syngas generated by the gasification of a carbon containing fuel (e.g., methane) to a gaseous product comprising CO and $H_2$, or emission streams from combustion processes, e.g., from carbon based electric generation power plants, or from flue gas stacks from such plants, industrial furnaces, stoves, ovens, or fireplaces or from airplane or car exhausts. A $CO_2$-containing gaseous phase may alternatively be from respiratory processes in mammals, living plants and other $CO_2$ emitting species, in particular from green-houses. A $CO_2$-containing gas phase may also be off-gas, from aerobic or anaerobic fermentation, such as brewing, fermentation to produce useful products such as ethanol, or the production of biogas. Such fermentation processes can occur at elevated temperatures if they are facilitated by thermophilic microorganisms, this is for example seen in the production of biogas. A $CO_2$-containing gaseous phase may alternatively be a gaseous phase enriched in $CO_2$ for the purpose of use or storage. The above described gaseous phases, may also occur as multiphase mixtures, where the gas co-exist with a certain degree of fluids (e.g., water or other solvents) and/or solid materials (e.g., ash or other particles). $CO_2$-containing liquids are any solution or fluid, in particular aqueous liquids, containing measurable amounts of $CO_2$, preferably at one of the levels mentioned above. $CO_2$-containing liquids may be obtained by passing a $CO_2$-containing gas or solid (e.g., dry ice or soluble carbonate containing salt) into the liquid. $CO_2$-containing fluids may also be compressed $CO_2$ liquid (that contains contaminants, such as dry-cleaning fluid), or supercritical $CO_2$, or $CO_2$ solvent liquids, like ionic liquids.

The term "$CO_2$ extraction" is to be understood as a reduction of $CO_2$ from a $CO_2$-containing medium. Such an extraction may be performed from one medium to another, e.g., gas to liquid, liquid to gas, gas to liquid to gas, liquid to liquid or liquid to solid, but the extraction may also be the conversion of $CO_2$ to bicarbonate or carbonate within the same medium. The term $CO_2$ capture is also used to indicate extraction of $CO_2$ from one medium to another or conversion of $CO_2$ to bicarbonate or carbonate.

When used herein the term "coding sequence" indicates a nucleotide sequence, which directly specifies the amino acid sequence of its protein product. The boundaries of the coding sequence are generally determined by an open reading frame, which usually begins with the ATG start codon or alternative start codons such as GTG and TTG. The coding sequence may be a DNA, cDNA, mRNA, or recombinant nucleotide sequence.

The term "functional fragment of a polypeptide" is used to describe a polypeptide which is derived from a longer polypeptide, e.g., a mature polypeptide, and which has been truncated either in the N-terminal region or the C-terminal region or in both regions to generate a fragment of the parent polypeptide. To be a functional polypeptide the fragment must maintain at least 20%, preferably at least 40%, more preferably at least 50%, more preferably at least 60%, more preferably at least 70%, more preferably at least 80%, even more preferably at least 90%, most preferably at least 95%, and even most preferably at least 100% of the CA activity of the parent polypeptide.

The term "fungal origin" includes molecules such as polypeptides, nucleic acids, DNA and RNA derived from fungi. It is also intended to include modified or mutated molecules where the parent molecule originally was derived from bacteria. The origin of the modified or mutated molecule should still be recognizable, preferably polypeptide and nucleic acid sequences are at least 60% identical to the parent molecule, more preferably it is at least 65%, 70%, 75%, 80%, 85%, 90%, 95%, 96%, 97%, 98% or 99% identical to the parent molecule.

The term "identity" is used to describe the relatedness between two amino acid sequences or two nucleic acid sequences. For purposes of the present invention, the alignment of two amino acid sequences is determined by using the Needle program from the EMBOSS package (http://emboss.org) version 2.8.0. The Needle program implements the global alignment algorithm described in Needleman and Wunsch, 1970, *J. Mol. Biol.* 48: 443-453. The substitution matrix used is BLOSUM62, gap opening penalty is 10, and gap extension penalty is 0.5. The degree of identity between two amino acid sequences is calculated as the number of exact matches in an alignment of the two sequences, divided by the length of the shortest sequence. The result is expressed in percent identity. An exact match occurs when the "first sequence" and the "second sequence" have identical amino acid residues in the same positions of the overlap (in the alignment example below this is represented by "I"). In the purely hypothetical alignment example below, the overlap is the amino acid sequence "HTWGERNL" of Sequence 1; or the amino acid sequence "HGWGEDANL" of Sequence 2. In the example a gap is indicated by a "-"

```
Sequence 1:  ACMSHTWGER-NL         (SEQ ID NO: 17)
                 | |||  ||
Sequence 2:      HGWGEDANLAMNPS    (SEQ ID NO: 18)
```

The degree of identity between two nucleotide sequences is determined using the same algorithm, software package and settings as described above.

The term "expression" includes any step involved in the production of the polypeptide including, but not limited to, transcription, post-transcriptional modification, translation, post-translational modification, and secretion.

The term "expression vector" is defined herein as a linear or circular DNA molecule that comprises a polynucleotide encoding a polypeptide of the invention, and which is operably linked to additional nucleotides that provide for its expression.

The term "heat-stable" or "thermostable" as used herein in reference to an enzyme, such as a carbonic anhydrase, indicates that the enzyme is functional or active (i.e., can perform catalysis) at an elevated temperature, i.e., above 45° C., preferably above 50° C., more preferably above 55° C., more preferably above 60° C., even more preferably above 65° C., most preferably above 70° C., most preferably above 80° C., most preferably above 90° C., and even most preferably above 100° C. The temperature stability of the carbonic anhydrase can be increased to some extent by way of formulation, e.g., by immobilization of the enzyme. In order for an enzyme to be considered as heat-stable it remains active for at least 15 minutes, preferably for at least 2 hours, more preferably for at least 24 hours, more preferably for at least 7 days, even more preferably for at least 14 days, most preferably for at least 30 days, even most preferably for at least 50 days at the elevated temperature. Generally, the level of activity is measured after the given time at the elevated temperature. The activity may be compared with the enzyme activity prior to the temperature elevation. Preferably, the activity is at least 40% after the given time at the elevated temperature, more preferably the activity is at least 50% after the given time at the elevated temperature, more preferably the activity is at least 60% after the given time at the elevated temperature, even more preferably the activity is at least 70% after the given time at the elevated temperature, most preferably the activity is at least 80% after the given time at the elevated temperature, even most preferably the activity is at least 90%, and absolutely most preferred the level of activity is at least equal to or unchanged after the given time at the elevated temperature.

The term "host cell", as used herein, includes any cell type which is susceptible to transformation, transfection, transduction, and the like with a nucleic acid construct comprising a polynucleotide of the present invention.

The term "isolated polypeptide" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

The term "operably linked" denotes herein a configuration in which a control sequence is placed at an appropriate position relative to the coding sequence of the polynucleotide sequence such that the control sequence directs the expression of the coding sequence of a polypeptide.

The term "region of nucleotide sequence encoding a mature polypeptide" as used herein means the region of a nucleotide sequence counting from the triplet encoding the first amino acid of a mature polypeptide to the last triplet encoding the last amino acid of a mature polypeptide.

The term "polypeptide fragment" is defined herein as a polypeptide having one or more amino acids deleted from the amino and/or carboxyl terminus of a sequence of the present invention or a homologous sequence thereof, wherein the fragment has CA activity.

The term "secreted polypeptide" as used herein is to be understood as a polypeptide which after expression in a cell is either transported to and released to the surrounding extracellular medium or is associated/embedded in the cellular membrane so that at least a part of the polypeptide is exposed to the surrounding extracellular medium.

The term "substantially pure polypeptide" denotes herein a polypeptide preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides of the present invention are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

Herein, the term "substantially pure polypeptide" is synonymous with the terms "isolated polypeptide" and "polypeptide in isolated form".

The term "Syngas" or "synthesis gas" is used to describe a gas mixture that contains varying amounts of carbon monoxide and hydrogen generated by the gasification of a carbon containing fuel (e.g., methane or natural gas) to a gaseous product with a heating value. $CO_2$ is produced in the syngas reaction and must be removed to increase the heating value.

The term "thermophilic" in relation to an organism, describes an organism which thrives at relatively high temperatures, i.e., above 45° C. Hyperthermophilic organisms thrive in extremely hot environments, that is, hotter than around 60° C. with an optimal temperature above 80° C.

Use of Heat-Stable Carbonic Anhydrases

Currently, two heat-stable carbonic anhydrase are known, namely the beta-class CA (Cab) from *Methanobacterium thermoautotrophicum* ΔH, which has been reported to be heat stable to up to 75° C. (Smith and Ferry, 1999, *J. Bacteriol.* 181: 6247-6253) and the gamma-class carbonic anhydrase (Cam) from *Methanosarcina thermophila* TM-1. Cam was isolated for the first time in 1994 (Alber and Ferry, 1994, *Proc. Natl. Acad. Sci. USA* 91: 6909-1913), and in 1996 it was shown to be stable to heating at 55° C. for 15 min (Alber and Ferry, 1996, *J. Bacteriol.* 178: 3270-3274). Cam is the only isolated enzyme of the gamma-class, and has been subject to a lot of characterization studies since its discovery. However, it has never been suggested to exploit the thermostability of these enzymes in any technical uses. US 2004/0259231 discloses the use of Cam as well as the non-thermostable human CA isoform IV in a $CO_2$ solubilization and concentration process, there is however no indication that Cam is preferable over CA-IV.

To our knowledge, no heat-stable alpha-class carbonic anhydrases isolated from an organism occurring in nature (naturally occurring heat-stable alpha-carbonic anhydrase) have been described until this day. US 2006/0257990 describes variants of human carbonic anhydrase II with a certain degree of thermostability.

One aspect of the present invention is the technical application of heat-stable carbonic anhydrases in the extraction of $CO_2$ from a $CO_2$-containing medium, such as a gas, a liquid, or multiphase mixture. Preferably, the $CO_2$ is extracted to another medium such as a gas or liquid separated from the first medium, but the extraction may also be the conversion of $CO_2$ to bicarbonate within the same medium. The present invention is in particular useful where the temperature of the $CO_2$-containing medium is above the temperature optimum for commercially available carbonic anhydrases, such as CA-I or CA-II isolated from human or bovine erythrocytes, which have temperature optimums at approximately 37° C.

In one embodiment of the present invention the heat-stable carbonic anhydrase to be applied in the extraction of $CO_2$ is of bacterial or archaeal or fungal origin, except for the gamma-class carbonic anhydrase from *Methanosarcina thermophila* TM-1 (DSM 1825). In another embodiment the carbonic anhydrases to be applied in the extraction of $CO_2$ may be from any of the distinct CA classes; alpha, or beta, or gamma, preferably they belong to the alpha- or beta-class.

In another embodiment the carbonic anhydrases to be applied in the extraction of $CO_2$ belong to the alpha-class, in particular a naturally occurring alpha-class carbonic anhydrase is preferred. Other preferred heat-stable carbonic anhydrases for use in the present invention are those which are at least 60%, 65%, 70%, 75%, 80%, 85%, 90%, 95%, 96%, 97%, 98%, 99% or 100% identical with a carbonic anhydrase selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14 and SEQ ID NO: 16 or from *Bacillus clausii* KSM-K16 (NCBI acc. No. Q5WD44) or from *Bacillus halodurans* (NCBI acc. No. Q9KFW1). Alpha-class carbonic anhydrases are generally monomers, are inhibited by sulfonamides and posses esterase activity (human CA-III is an exception, since this isomer is insensitive to sulfonamides and does not hydrolyze p-nitrophenylacetate). Further, alpha-carbonic anhydrases are identified by their consensus sequence motif: S-E-[HN]-x-[LIVM]-x(4)-

[FYH]-x(2)-E-[LIVMGA]-H-[LIVMFA](2). The alpha-carbonic anhydrases are generally secreted which is an advantage when expression in industrial scale is needed. Further, alpha-class carbonic anhydrases is the CA-class with the highest turnover of up to $10^5$ molecules of $CO_2$ per second. An enzyme with a high activity is generally an advantage, since the amount of enzyme needed may be reduced or the process is more expedite than with a less active enzyme.

In another embodiment the carbonic anhydrases to be applied in the extraction of $CO_2$ belong to the beta-class. Preferred heat-stable beta-carbonic anhydrases for use in the present invention are those which are at least 60%, 65%, 70%, 75%, 80%, 85%, 90%, 95%, 96%, 97%, 98%, 99% or 100% identical with a carbonic anhydrase selected from the group consisting of beta-carbonic anhydrase from *Methanobacterium thermoautotrophicum* ΔH (NCBI acc. No. Q50565), beta-class carbonic anhydrase from *Bacillus clausii* KSM-K16 (NCBI acc. No. YP_176370/Q5WE01), beta-carbonic anhydrase from *Bacillus halodurans* (NCBI acc. No. NP_244152/Q9K7S3), and beta-carbonic anhydrases from *Aspergillus fumigatus* (NCBI acc. NO Q4WPJ0, A4DA32, Q4WQ18 or A4DA31). Beta-class carbonic anhydrase exist as dimers, tetramers, hexamers and octamers. Generally, beta-carbonic anhydrases are intracellular proteins, and their turnover approximately $2 \times 10^4$ molecules of $CO_2$ per second. Some beta-carbonic anhydrases can also be identified by the following consensus sequence motif: C-[SA]-D-S-R-[LIVM]-x-[AP] as disclosed on the Expasy homepage under prosite documentation number PD0000586 (www.expasy.org/cgi-bin/prosite-search-ac?PD0000586).

In a further embodiment the carbonic anhydrase to be applied in the extraction of $CO_2$ belong to the gamma-class carbonic anhydrase, except for the carbonic anhydrase from *Methanosarcina thermophila* strain TM-1 (DSM 1825) (Cam) (Alber and Ferry, 1994, Proc. Natl. Acad. Sci. USA 91: 6909-6913). Gamma-class carbonic anhydrases are trimeric, 1000-10000 fold less sensitive to sulfonamides and do not possess esterase activity. Some gamma-carbonic anhydrases are known to be secreted, and their turnover is up to $7 \times 10^4$ molecules of $CO_2$ per second. Generally, the gamma-class carbonic anhydrase is a very diverse group of proteins that share the sequence motif characteristic of the left-handed parallel beta-helix (OH) fold (Parisi et al., 2000, *Molecular Phylogenetics and Evolution* 12: 323-334).

In particular carbonic anhydrase, especially heat-stable carbonic anhydrase, may be used for carbon dioxide extraction from $CO_2$ emission streams, e.g., from carbon-based or hydrocarbon-based combustion in electric generation power plants, or from flue gas stacks from such plants, industrial furnaces, stoves, ovens, or fireplaces or from airplane or car exhausts. Carbonic anhydrases, in particular heat-stable carbonic anhydrases, may also be used to remove $CO_2$ in the preparation of industrial gases such as acetylene ($C_2H_2$), carbon monoxide (CO), chlorine ($Cl_2$), hydrogen ($H_2$), methane ($CH_4$), nitrous oxide ($N_2O$), propane ($C_3H_8$), sulfur dioxide ($SO_2$), argon (Ar), nitrogen ($N_2$), and oxygen ($O_2$). Carbonic anhydrase can also be used to remove $CO_2$ from a raw natural gas during the processing to natural gas. Removal of $CO_2$ from the raw natural gas will serve to enrich the methane ($CH_4$) content in the natural gas, thereby increasing the thermal units/$m^3$. Raw natural gas is generally obtained from oil wells, gas wells, and condensate wells. Natural gas contains between 3 to 10% $CO_2$ when obtained from geological natural gas reservoirs by conventional methods. Carbonic anhydrase can also be used to purify the natural gas such that it is substantially free of $CO_2$, e.g., such that the $CO_2$ content is below 1%, preferably below 0.5%, 0.2%, 0.1%, 0.05% and most preferably below 0.02%. In resemblance to the methane enrichment of natural gases, carbonic anhydrases can also be used to enrich the methane content in biogases. Biogases will always contain a considerable degree of $CO_2$, since the bacteria used in the fermentation process produce methane (60-70%) and $CO_2$ (30-40%). Biogas production may be performed using mesophilic or thermophilic microorganisms. The process temperatures for mesophilic strains is approximately between 25° C. and 40° C., preferably between 30° C. and 35° C. In this temperature range a carbonic anhydrase may be of bovine or human origin since there are no requirements to thermostability of the enzyme. However, a carbonic anhydrase that tolerates higher temperatures will offer improved robustness in actual use and storage related to biogas processes utilizing mesophilic strains. Thermophilic strains allow the fermentation to occur at elevated temperatures, e.g., from 40° C. to 80° C., and preferably from 50° C. to 70° C. and even more preferably from 55° C. to 60° C. In such processes a heat-stable carbonic anhydrase is particularly useful to remove $CO_2$ from the methane. The present invention provides for the use of a carbonic anhydrase to reduce the carbon dioxide content in a biogas, preferably the $CO_2$ content is reduced such that it constitutes less than 25%, more preferably less than 20%, 15%, 10%, 5%, 2%, 1%, 0.5% and most preferably less than 0.1%. In a preferred embodiment the carbonic anhydrase is heat-stable. Furthermore, carbonic anhydrase may be applied in the production of syngas by removing the $CO_2$ generated by the gasification of a carbon containing fuel (e.g., methane or natural gas) thereby enriching the CO, $H_2$ content of the syngas. Where syngas production occurs at elevated temperatures the use of a heat-stable carbonic anhydrase is an advantage. The present invention provides for the use of a carbonic anhydrase to reduce the carbon dioxide content in a syngas production. Preferably, the $CO_2$ content is reduced such that it constitutes less than 25%, more preferably less than 20%, 15%, 10%, 5%, 2%, 1%, 0.5% and most preferably less than 0.1%. In a preferred embodiment the carbonic anhydrase is heat-stable. Preferably, the carbonic anhydrases to be used for $CO_2$ extraction as described above maintain activity at temperatures above 45° C., preferably above 50° C., more preferably above 55° C., more preferably above 60° C., even more preferably above 65° C., most preferably above 70° C., most preferably above 80° C., most preferably above 90° C., and even most preferably above 100° C. for at least 15 minutes, preferably for at least 2 hours, more preferably for at least 24 hours, more preferably for at least 7 days, even more preferably for at least 14 days, most preferably for at least 30 days, even most preferably for at least 50 days at the elevated temperature. The temperature stability of the carbonic anhydrase can be increased to some extent by way of formulation, e.g., by immobilization of the enzyme.

In an aspect of the present invention the $CO_2$ extraction from a $CO_2$-containing medium is performed in enzyme based bioreactors. Before the carbon dioxide-containing medium is processed in a bioreactor, it may be purified to free it from contaminants which may disturb the enzymatic reaction or interfere with bioreactor functionality in other ways, e.g., by clotting outlets or membranes. Gasses/multiphase mixtures emitted from combustion processes, e.g., flue gases or exhausts, are preferably cleared of ash, particles, $NO_x$ and/or $SO_2$, before the gas/multiphase mixture is passed into the bioreactor. The raw natural gas from different regions may have different compositions and separation requirements. Preferably, oil, condensate, water and natural gas liquids, if present in the raw natural gas, are removed prior to the extraction of $CO_2$ in an enzyme based bioreactor. The $CO_2$ from the raw natural gas may be extracted in the same process as the sulfur removal, or it may be extracted in a completely separate process. If the gas at this point exceeds the temperature optimum of the carbonic anhydrase of the present invention, some degree of cooling may be needed. Preferably, the reaction temperature is between 45° C. and 100° C., more preferably between 45° C. and 80° C., even more preferably between 45° C. and 60° C., and most preferably between 45° C. and 55° C. However, due to the thermostability of the enzymes of the present invention, the need for cooling is at least 5° C. less than if a CA-I or CA-II isolated from human or bovine erythrocytes is applied in the bioreactor.

One type of bioreactor useful with the present invention is based on a process in which a mixed gas stream (e.g., containing oxygen, nitrogen and carbon dioxide) contacts the enzyme, carbonic anhydrase, at a gas-liquid interface to catalyze the conversion of carbon dioxide contained in the gas to bicarbonate or carbonate. The gas-liquid interface in such a bioreactor can for example be provided by an enzyme based hollow fiber membrane bioreactor (HFMB). An example of HFMB is a hollow fiber contained liquid membrane (HF-CLM) as described by Majumdar et al., 1988, AIChE 1135-1145. CLMs are made by sandwiching a core liquid between two polymer membranes. The core liquid is preferably continuously re-supplied through a reservoir of liquid membrane solvent. An alternative type of enzyme based CLM permeator useful in a bioreactor is described in Cowan et al., 2003, *Ann. NY Acad. Sci.* 984: 453-469 (hereby incorporated by reference). In summary, the bioreactor of this reference comprise a liquid membrane constructed by sandwiching a carbonic anhydrase containing phosphate buffered solution between two hydrophobic, microporous, polypropylene membranes (e.g., Celgard PP-2400). The CA concentration is preferably between 100-166 micro-M, and the buffer has a phosphate concentration between 50-75 mM and a pH between 6.4 and 8.0. Preferred concentrations of CA and of buffer are a function of the feed $CO_2$ concentration. The pH optimum is a function of the $CO_2$ concentration and the buffer strength. The thickness of the aqueous phase is preferably 330 micro-m, but may be varied from 70 micro-m to 670 micro-m by the use of annular spacers. Preferred membrane thickness is determined principally by the desired selectivity towards other gases such as $NO_2$ or $O_2$ and secondarily by desired permeance. The liquid membrane fluid volume is maintained by hydrostatic fluid addition from a reservoir, ensuring a constant liquid membrane thickness and prevents separation between the polymer membrane and the metal support. One side of the CLM (the feed membrane) is contacted with a $CO_2$-containing feed gas stream, and the other side of the CLM (the sweep membrane) is in contact with a $CO_2$-free sweep gas stream, for example argon. In this bioreactor $CO_2$ from the feed gas stream is converted to bicarbonate in the liquid phase and then returned as $CO_2$ to the sweep gas stream from where it can be stored in the form of compressed $CO_2$. The entire process is catalysed by the carbonic anhydrase. The CLM permator described above is capable of capturing $CO_2$ from feed gas streams with down to 0.1% $CO_2$. Alternative CLM permators are composed of hollow-fiber membrane mats, e.g., Celgard X40-200 or X30-240 instead of hydrophobic, microporous, polypropylene membranes. The same CA concentration, buffer concentration and pH can be used with hollow-fiber CLMs. The hollow-fiber permeator can be arranged into different designs. In one design the permeator is arranged much like a heat exchanger and consists of multiple sets of hollow fiber feed fibers and hollow fiber sweep fibers arranged orthogonally while a carrier fluid fills the space between the feed and sweep fiber bundles (see for example Majumdar et al., 1988, AIChE 1135-1145). Another design is a spiral wound hollow fiber design that can operate in either co-current or counter-current mode. WO 04/104160 describes these and other hollow-fiber permator designs in more detail, see in particular FIGS. 1 to 14 (hereby incorporated by reference). WO 04/104160 describes the use of a phosphate buffer as the membrane liquid. When carbonic anhydrase is added to the membrane liquid it was either dissolved in phosphate buffer or 1 M $NaHCO_3$.

The present inventors have realized that when using a bicarbonate buffer as the membrane liquid the pH of the buffer is important for the amount of $CO_2$ that can be extracted from the flue gas. An increase in the pH of the bicarbonate solution increases the rate of the hydration of carbon dioxide to bicarbonate. In a preferred embodiment of the present invention the membrane liquid is a bicarbonate buffer, such as sodium bicarbonate, potassium bicarbonate, cesium bicarbonate or another suitable salt of the bicarbonate. The pH of the bicarbonate buffer is preferably above 8.5, more preferably above 9.0 and even more preferably above 9.5, even more preferred above 9.95, and most preferably above 10.5 or above pH 11. The increase of the buffer pH allows for a reduction in the amount of carbonic anhydrases needed to extract $CO_2$ from the feed gas. Preferably the amount of carbonic anhydrase is below 2 g enzyme protein/L membrane liquid, more preferably it is below 1.5 g/L, even more preferably below 1 g/L, even more preferably below 0.6 g/L, even more preferably below 0.3 g/L and even more preferably below 0.1 g/L, and most preferably below 0.01 g/L, and even most preferably below 0.001 g/L.

Another type of bioreactor which may be useful in the present invention is based on a process in which a gas phase or multiphase mixture, is contacted with a liquid phase under conditions where the $CO_2$ in the gas phase is absorbed by the liquid phase where it is converted into bicarbonate by carbonic anhydrase. Preferably, the reaction temperature is between 45° C. and 100° C., more preferably between 45° C. and 80° C., even more preferably between 45° C. and 60° C., and most preferably between 45° C. and 55° C. The bicarbonate enriched liquid is removed from the reactor by a continuous flow, to ensure that the equilibrium between $CO_2$ and bicarbonate is shifted towards continuous conversion of $CO_2$. The gas phase dissolution into the liquid phase is dependent on the surface contact area between the gas and liquid. A large contact area can either be achieved by passing liquid and $CO_2$-containing gas through a packed column or by bubbling the $CO_2$-containing gas through the liquid generating an elevated pressure in the reaction chamber. Reactors of these types are described in U.S. Pat. No. 6,524,843 and WO 2004/007058, respectively; both references are hereby incorporated in their entirety. In summary, packed columns can be composed of packings such as raschig rings, berl saddles, intalox metal, intalox saddles, pall rings. The packing materials may be a polymer such as nylon, polystyrene a polyethylene, a ceramic such as silica, or a metal such as aluminium. In both reactor types the liquid is continuously exchanged, hence carbonic anhydrase must be retained in the reactor by various means. In the packed columns the carbonic anhydrase can be immobilized on the packing material (for methods of immobilizing CA, see for example in WO 2005/114417). In the "bubbling" reactors the carbonic anhydrase can be entrapped in a porous substrate, for example, an insoluble gel particle such as silica, alginate, alginatelchitosane, algnate/carboxymethylcellulose, or the carbonic anhydrase can be immobilized on a solid packing (as in the packed columns) in suspension in the liquid, or the carbonic anhydrase can be chemically linked in an albumin or PEG network. When the reactors are in operation an aqueous or organic solvent enters the reactor at one end, preferably the top, and flows to the other end, preferably the bottom, and the $CO_2$-containing gas stream (feed gas) enters the reactor at one end, preferably at the opposite end of the solvent (the bottom) and the gas passes through the liquid and exits through a gas outlet at the opposite end (preferably, the top of the reactor). The solvent/liquid that exits the reactor is enriched in bicarbonate and the exit gas is reduced in the $CO_2$ content compared to the feed gas. The bicarbonate containing solution may be processed in subsequent reactions for example to generate pure $CO_2$ or carbonate precipitates such as $CaCO_3$. The exit gas may also be subjected to further rounds of $CO_2$ extraction. In a preferred embodiment of the present invention the reactor liquid is a bicarbonate buffer, such as sodium bicarbonate, potassium bicarbonate, cesium bicarbonate or another suitable salt of the bicarbonate. The pH of the bicarbonate buffer is preferably above 8.5, more preferably above 9.0 and even more preferably above 9.5, even more preferred above 9.95, and most preferably above 10.5 or above pH 11.

A third type of bioreactor which is useful in the present invention is described in U.S. Pat. No. 7,132,090, hereby incorporated by reference. In summary, gaseous $CO_2$, or $CO_2$ from a multiphase mixture is diffused into a capturing liquid by allowing the gaseous $CO_2$ to pass through a gas diffusion membrane. The $CO_2$ may pass into the liquid by diffusion (pressure aided) or the transfer may be aided by a carbonic anhydrase immobilized on the diffusion membrane, e.g., by cross-linking or by affixing a gel or polymer matrix containing the carbonic anhydrase onto the diffusion membrane. Since the carbonic anhydrase reacts specifically with dissolved $CO_2$, it favors the movement of gaseous $CO_2$ into the fluid by accelerating the reaction of the dissolved $CO_2$ and water to form carbonic acid, thereby removing $CO_2$ rapidly and allowing the dissolution of $CO_2$ from the gas from the feed stream into the water to a greater extent than it would otherwise. Preferably, the gas diffusion membrane has a high surface area to facilitate a large flow of the gaseous $CO_2$ through the membrane. Suitable membranes include a polypropylene gas exchange membrane, ePTFE (GORE-TEX), Nafion membranes, zeolites, chytosan, polyvinylpyrollindine, cellulose acetate, and immobilized liquid membranes. The $CO_2$/bicarbonate rich fluid that emerges from the gas diffusion membrane is passed by a matrix that contains carbonic anhydrase. Preferably, the matrix is contained in a chamber which is separate from the chamber containing the diffusion membrane. Examples of suitable matrixes include beads, fabrics, fibers, membranes, particulates, porous surfaces, rods, and tubes. Specific examples of suitable matrixes include alumina, bentonite, biopolymers, calcium carbonate, calcium phosphate gel, carbon, cellulose, ceramic supports, clay, collagen, glass, hydroxyapatite, ion-exchange resins, kaolin, nylon, phenolic polymers, polyaminostyrene, polyacrylamide, polypropylene, polymerhydrogels, sephadex, sepharose, silica gel, and TEFLON-brand PTFE. The carbonic anhydrase may be immobilized to the matrix or entrapped within it. Once the $CO_2$ is passed into the liquid an equilibrium between carbonic acid, bicarbonate and carbonate ions will be established, a process which is catalyzed by carbonic anhydrase. Base (e.g., $OH^-$ ions) can then be added to shift the equilibrium to favor the formation of carbonate ions. In the final step, a mineral ion is added to a solution to precipitate carbonate salts. Alternatively, no base is added, thereby predominantly generating bicarbonate ion which can be concentrated using an ion-exchange resin or membrane. The bicarbonate can then be precipitated using sodium, magnesium or calcium ions. In a preferred embodiment of the present invention the capturing liquid is a bicarbonate buffer, such as sodium bicarbonate, potassium bicarbonate, cesium bicarbonate or another suitable salt of the bicarbonate. The pH of the bicarbonate buffer is preferably above 8.5, more preferably above 9.0 and even more preferably above 9.5, even more preferred above 9.95, and most preferably above 10.5 or above pH 11. In a preferred embodiment of the present invention the bioreactor operates in steady-state conditions whereby the $CO_2$ uptake rate improvement provided by carbonic anhydrase results in overall efficiency improvement of the bioreactor.

The enzyme based bioreactors described above, including a heat-stable carbonic anhydrase of the present invention, also find more unconventional applications such as in pilot cockpits, submarine vessels, aquatic gear, safety and firefighting gear and astronaut's space suits to keep breathing air free of toxic $CO_2$ levels. Other applications are to remove $CO_2$ from confined spaces, such as to reduce hazardous $CO_2$ levels from inside breweries and enclosed buildings carrying out fermentation, and from $CO_2$ sensitive environments like museums and libraries, to prevent excessive $CO_2$ from causing acid damage to books and artwork.

Carbonic anhydrase can be used as an independent $CO_2$ extraction catalyst or it may alternatively be combined with conventional $CO_2$ extraction technologies such as chemical absorption via amine-based solvents or aqueous ammonia or physical solvents such as Selexol™ (Union Carbide) or polyethylene glycol ethers. The present inventors have shown that by adding carbonic anhydrase to a MEA solution the efficiency of the scrubbing is significantly increased. In a further embodiment of the present invention a carbonic anhydrase, preferably a heat-stable carbonic anhydrase, is combined with a carbon dioxide absorbing compound such as amine-based compounds such as aqueous alkanolamines including monoethanolamine (MEA), diethanolamine (DEA), methyldiethanolamine (MDEA), 2-amino-2-methyl-1-propanol (AMP), 2-amino-2-hydroxymethyl-1,3-propanediol (AHPD) or other primary, secondary, tertiary or hindered amine-based solvents, or aqueous salts of glycine and taurine or other liquid absorbers such as aqueous NaOH, KOH, LiOH, carbonate or bicarbonate solutions at different ionic strengths or aqueous electrolyte solutions and promoters such as piperazine, or polyethylene glycol ethers, or a blend of them or analogs or blends thereof. The combination may either be applied in the bioreactors described above or it may be applied to already existing $CO_2$ scrubbing facilities based on more conventional techniques. In conventional bioreactors, the concentration of alkanolamines is typically 15-30 weight percent. In conventional processes, proprietary inhibitors, such as Fluor Daniel's EconAmine, are added to provide for increasing the amine concentration while reducing the risk of corrosion. In the bioreactors described above, the concentration of alkanolamines is preferably below 15% (V/V), more preferably below 12%, 10%, 8%, 6%, 5%, 4%, 3%, 2%, 1%, 0.5%, 0.2% and most preferably below 0.1% (V/V).

Another aspect of the present invention relates to biogas production where the $CO_2$ extraction is performed directly in the biogas fermentation broth, as an alternative to passing the biogas through a bioreactor as described above. By adding carbonic anhydrase to the anaerobic broth, more $CO_2$ from the gas phase can be converted into bicarbonate, which is the substrate for methane production by the methanogenic Archaea. It has been shown for *Methanosarcina thermophila* TM-1 that bicarbonate may be a limiting factor for the methane production, for example cultures of *M. thermophila* ™-1 grown in low bicarbonate solution (0.6 mM) showed a considerable lag phase (i.e., methane production began later) when compared with cultures containing ten times higher bicarbonate dosages (6 mM). Additionally, the total yield of methane was 25 times less at the lower bicarbonate dosage (Murray and Zinder, 1985, *Appl. Environ. Microbiol.* 50: 49-55).

Another aspect of the present invention is addition of carbonic anhydrase to a fermentation broth, in particular in cases where the bicarbonate concentration in the broth is a limiting factor. Addition of carbonic anhydrase can increase the methane production. Particularly, the genus *Methanosarcina* is frequently present in thermophilic biogas digesters (Mladenovska and Ahring, 2000, *FEMS Microbiol. Ecol.* 3: 225-229). Hence, a heat-stable carbonic anhydrase will be particularly useful if the biogas production is performed at elevated temperatures using one or more thermophilic microorganisms, for example methanogens like *Methanosarcina* sp. that can use $CO_2$/biocarbonate as carbon source for growth and methanogenesis.

A further embodiment of the present invention is use of a carbonic anhydrase, in particular a heat-stable carbonic anhydrase, as an additive in a biogas fermentation broth.

Polypeptides

A polypeptide sequence from *Bacillus clausii* KSM-K16 similar to the sequences of the present invention is disclosed in the NCBI database under acc. No. Q5WD44 (presented as SEQ ID NO: 14). The sequence is translated from a nucleotide sequence derived from a genomic sequencing project on *Bacillus clausii* KSM-K16, performed by Kao. Based on similarity to other alpha-class carbonic anhydrases the nucleotide sequence was assigned to this class, but it has to our knowledge never been expressed and characterized. Hence, the nucleotide sequence was cloned and the polypeptide was expressed for the first time in the examples of the present application, and it was shown that the polypeptide possess carbonic anhydrase activity after 15 minutes and 2 hours of heating to temperatures above 50° C.

An aspect of the present invention relates to novel heat-stable carbonic anhydrases of the alpha-class type. One embodiment relates to isolated polypeptides having an amino acid sequence which has a degree of identity of at least 97%, preferably at least 98%, more preferably at least 99%, most preferably at least 100% to the amino acid sequence of SEQ ID NO: 2, SEQ ID NO: 4, SEQ ID NO: 6, SEQ ID NO: 8, SEQ ID NO: 10, or SEQ ID NO: 12, which polypeptide have carbonic anhydrase activity (hereinafter "homologous polypeptides"). In a preferred embodiment, the homologous polypeptides have an amino acid sequence which differs by seven amino acids, preferably by five amino acids, more preferably by four amino acids, even more preferably by three amino acids, most preferably by two amino acids, and even most preferably by one amino acid from the amino acid sequence of SEQ ID NO: 2, SEQ ID NO: 4, SEQ ID NO: 6, SEQ ID NO: 8, SEQ ID NO: 10, or SEQ ID NO: 12. Polypeptides with amino acids of position 1 to 237 of SEQ ID NO: 2, SEQ ID NO: 4, SEQ ID NO: 6, SEQ ID NO: 8, SEQ ID NO: 10, or SEQ ID NO: 12 are mature polypeptides of the present invention. Polypeptides with amino acids of position 10 to 237 of SEQ ID NO: 2, SEQ ID NO: 4, SEQ ID NO: 6, SEQ ID NO: 8, SEQ ID NO: 10, or SEQ ID NO: 12 are recombinant polypeptides of the present invention. In a further preferred embodiment the homologous polypeptides of the present invention have carbonic anhydrase activity at an elevated temperature, i.e., above 45° C., preferably above 50° C., more preferably above 55° C., more preferably above 60° C., even more preferably above 65° C., most preferably above 70° C., most preferably above 80° C., most preferably above 90° C., and even most preferably above 100° C.

A polypeptide of the present invention preferably comprises, more preferably consists of, amino acids of a mature polypeptide or a recombinant polypeptide selected from the group consisting of SEQ ID NO: 2, SEQ ID NO: 4, SEQ ID NO: 6, SEQ ID NO: 8, SEQ ID NO: 10, and SEQ ID NO: 12 or an allelic variant thereof; or a fragment thereof that has carbonic anhydrase activity, preferably at an elevated temperature. In a preferred embodiment, a polypeptide comprises, preferably consists of, an amino acid sequence selected from the group consisting of SEQ ID NO: 2, SEQ ID NO: 4, SEQ ID NO: 6, SEQ ID NO: 8, SEQ ID NO: 10 and SEQ ID NO: 12. In another preferred embodiment, a polypeptide comprises, preferably consists of, amino acids 1 to 237 or 10 to 237 of an amino acid sequence selected from the group consisting of SEQ ID NO: 2, SEQ ID NO: 4, SEQ ID NO: 6, SEQ ID NO: 8, SEQ ID NO: 10 and SEQ ID NO: 12 or an allelic variant thereof; or a fragment thereof that has carbonic anhydrase activity, preferably at an elevated temperature. In an even more preferred embodiment, a polypeptide consists of amino acids 10 to 237 of an amino acid sequence selected from the group consisting of SEQ ID NO: 2, SEQ ID NO: 4, SEQ ID NO: 6, SEQ ID NO: 8, SEQ ID NO: 10 and SEQ ID NO: 12 and has the N-terminal amino acid sequence LKASW with a leucine as the most N-terminal amino acid, irrespective of the amino acid indicated in that position of the respective sequence.

In a further embodiment, the present invention relates to isolated polypeptides having carbonic anhydrase activity, preferably at an elevated temperature, which are encoded by polynucleotides which hybridize under very low stringency conditions, preferably low stringency conditions, more preferably medium stringency conditions, more preferably medium-high stringency conditions, even more preferably high stringency conditions, and most preferably very high stringency conditions with:

(i) nucleotides encoding a mature enzyme selected from the group consisting of SEQ ID NO: 2, SEQ ID NO: 4, SEQ ID NO: 6, SEQ ID NO: 8, SEQ ID NO: 10 and SEQ ID NO: 12, (ii) a polynucleotide sequence selected from the group consisting of regions of SEQ ID NO: 1, SEQ ID NO:3, SEQ ID NO: 5, SEQ ID NO: 7, SEQ ID NO: 9 and SEQ ID NO: 11 encoding a mature enzyme, (iii) the cDNA sequence contained in a polynucleotide sequence selected from the group consisting of regions of SEQ ID NO: 1, SEQ ID NO: 3, SEQ ID NO: 5, SEQ ID NO: 7, SEQ ID NO: 9 and SEQ ID NO: 11 encoding a mature enzyme, (iv) a subsequence of (i), (ii) or (iii) of at least 100 contiguous nucleotides, or (v) a complementary strand of (i), (ii), (iii), or (iv) (Sambrook, Fritsch, and Maniatis, 1989, *Molecular Cloning, A Laboratory Manual*, 2d edition, Cold Spring Harbor, N.Y.).

A subsequence of SEQ ID NO: 1, SEQ ID NO: 3, SEQ ID NO: 5, SEQ ID NO: 7, SEQ ID NO: 9, or SEQ ID NO: 11 contains at least 100 contiguous nucleotides or preferably at least 200 contiguous nucleotides. Moreover, the subsequence may encode a polypeptide fragment which has carbonic anhydrase activity, preferably at an elevated temperature.

A polynucleotide sequence selected from the group consisting of SEQ ID NO: 1, SEQ ID NO: 3, SEQ ID NO: 5, SEQ ID NO: 7, SEQ ID NO: 9 and SEQ ID NO: 11 or a subsequence thereof, as well as an amino acid sequence selected from the group consisting of SEQ ID NO: 2, SEQ ID NO: 4, SEQ ID NO: 6, SEQ ID NO: 8, SEQ ID NO: 10 and SEQ ID NO: 12 or a fragment thereof, may be used to design a nucleic acid probe to identify and clone DNA encoding polypeptides having carbonic anhydrase activity, preferably at an elevated temperature, from an organism expected to encode a carbonic anhydrase, according to methods well known in the art. Carbonic anhydrase producing organisms may be eukaryotes, including mammals, algae, fungi and plants, prokaryotes including bacterial strains of different genera or species as well as archaeon. Preferably, such an organism is thermophilic or hyperthermopilic. Even more preferred the polynucleotide is obtained from a thermophilic *Bacillus clausii* strain which is not *Bacillus clausii* KSM-K16. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such organisms may, therefore, be screened for DNA which hybridizes with the probes described above and which encodes a polypeptide having carbonic anhydrase activity, preferably at an elevated temperature. Genomic or other DNA from such organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with a sequence selected from the group consisting of SEQ ID NO: 1, SEQ ID NO: 3, SEQ ID NO: 5, SEQ ID NO: 7, SEQ ID NO: 9 and SEQ ID NO: 11 or a subsequence thereof, the carrier material is used in a Southern blot.

For purposes of the present invention, hybridization indicates that a nucleotide sequence hybridizes to a labelled nucleic acid probe corresponding to the nucleotide sequence shown in SEQ ID NO: 1, SEQ ID NO: 3, SEQ ID NO: 5, SEQ ID NO: 7, SEQ ID NO: 9, or SEQ ID NO: 11 its complementary strand, or a subsequence thereof, under very low to very high stringency conditions. Molecules to which the nucleic acid probe hybridizes under these conditions can be detected using X-ray film.

In a preferred embodiment, the nucleic acid probe is nucleotides 1 to 237, nucleotides 238 to 474, nucleotides 475 to 711, of SEQ ID NO: 1, SEQ ID NO: 3, SEQ ID NO: 5, SEQ ID NO: 7, SEQ ID NO: 9, or SEQ ID NO: 11. In another preferred aspect, the nucleic acid probe is a polynucleotide sequence which encodes the polypeptide of SEQ ID NO: 2, SEQ ID NO: 4, SEQ ID NO: 6, SEQ ID NO: 8, SEQ ID NO: 10, or SEQ ID NO: 12 or a subsequence thereof. In another preferred aspect, the nucleic acid probe is the mature polypeptide coding region of SEQ ID NO: 1, SEQ ID NO: 3, SEQ ID NO: 5, SEQ ID NO: 7, SEQ ID NO: 9, or SEQ ID NO: 11.

For long probes of at least 100 nucleotides in length, very low to very high stringency conditions are defined as prehybridization and hybridization at 42° C. in 5×SSPE, 0.3% SDS, 200 micro-g/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency). In a particular embodiment, the wash is conducted using 0.2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency). In another particular embodiment, the wash is conducted using 0.1×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$, using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures. The carrier material is washed once in 6×SCC plus 0.1% SDS for 15 minutes and twice each for 15 minutes using 6×SSC at 5° C. to 10° C. below the calculated $T_m$.

In another aspect, the present invention relates to artificial variants comprising a conservative substitution, deletion, and/or insertion of one or more amino acids has been made to an amino acid sequence comprising or consisting of SEQ ID NO: 2, SEQ ID NO: 4, SEQ ID NO: 6, SEQ ID NO: 8, SEQ ID NO: 10, or SEQ ID NO: 12 or the mature or recombinant polypeptide thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain. Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by Neurath and Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly. In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Essential amino acids in the parent polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for biological activity (i.e., carbonic anhydrase activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. A large number of these analyses have already been performed on carbonic anhydrases, the most important are for example reviewed in Tripp et al., 2001, *J. Biol. Chem.* 276: 48615-48618 and Lindskog, 1997, *Pharmacol. Ther.* 74: 1-20. The identities of essential amino acids can also be inferred from analysis of identities with polypeptides which are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30:10832-10837; U.S. Pat. No. 5,223,409; WO 92/06204), and region-directed mutagenesis (Derbyshire et al., 1986, *Gene* 46:145; Ner et al., 1988, *DNA* 7:127).

Mutagenesis/shuffling methods can be combined with high-throughput, automated screening methods to detect activity of cloned, mutagenized polypeptides expressed by host cells. Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

One embodiment of the present invention is an isolated polypeptide having carbonic anhydrase activity at elevated temperatures selected from the group consisting of: (a) a polypeptide having an amino acid sequence which has at least 94% identity with the amino acid sequence of SEQ ID NO: 2 or SEQ ID NO: 4, or at least 91% identity with the amino acid sequence of SEQ ID NO: 6, or at least 96% identity with the amino acid sequence of SEQ ID NO: 8, or at least 89% identity with the amino acid sequence of SEQ ID NO: 10, or at least 97% identity with the amino acid sequence of SEQ ID NO: 12; (b) a polypeptide encoded by a nucleic acid sequence which hybridizes under medium stringency conditions with: (i) nucleotides encoding a mature polypeptide selected from the group consisting of SEQ ID NO: 2, SEQ ID NO: 4, SEQ ID NO: 6, SEQ ID NO: 8, SEQ ID NO: 10 and SEQ ID NO: 12, (ii) a polynucleotide sequence selected from the group consisting of regions of SEQ ID NO: 1, SEQ ID NO:3, SEQ ID NO: 5, SEQ ID NO: 7, SEQ ID NO: 9 and SEQ ID NO: 11 encoding a mature enzyme, (iii) the cDNA sequence contained in a polynucleotide sequence selected from the group consisting of regions of SEQ ID NO: 1, SEQ ID NO: 3, SEQ ID NO: 5, SEQ ID NO: 7, SEQ ID NO: 9 and SEQ ID NO: 11 encoding a mature enzyme, (iv) a subsequence of (i) or (ii) of at least 100 contiguous nucleotides, or (v) a complementary strand of (i), (ii), (iii) or (iv); and (c) a fragment of (a) or (b) having carbonic anhydrase activity.

A particular embodiment of the present invention relates to an isolated polypeptide having carbonic anhydrase activity at elevated temperatures selected from the group consisting of: (a) a polypeptide having an amino acid sequence which has at least 94%, preferably at least 96%, more preferred at least 98%, even more preferred at least 99% and most preferred at least 100% identity with the amino acid sequence of SEQ ID NO: 2 or SEQ ID NO: 4, or a functional fragment thereof; (b) a polypeptide encoded by a nucleic acid sequence which hybridizes under medium stringency conditions with: (i) nucleotides encoding a mature polypeptide of regions of SEQ ID NO: 2 or SEQ ID NO: 4, (ii) a polynucleotide sequence of SEQ ID NO: 1 or SEQ ID NO:3 encoding a mature enzyme, (iii) the cDNA sequence contained in a polynucleotide sequence of regions of SEQ ID NO: 1 or SEQ ID NO: 3 encoding a mature enzyme, (iv) a subsequence of (i) or (ii) of at least 100 contiguous nucleotides, or (v) a complementary strand of (i), (ii), (iii) or (iv); and (c) a fragment of (a) or (b) having carbonic anhydrase activity at elevated temperatures. In a preferred embodiment, the polypeptide has an amino acid sequence which differs by eleven amino acids, preferably by nine amino acids, more preferred by seven amino acids, more preferably by five amino acids, even more preferably by three amino acids, and most preferably by one amino acid from the amino acid sequence of SEQ ID NO: 2 or SEQ ID NO: 4.

Another particular embodiment of the present invention relates to an isolated polypeptide having carbonic anhydrase activity at elevated temperatures selected from the group consisting of: (a) a polypeptide having an amino acid sequence which has at least 91%, preferably at least 94%, more preferred at least 96%, even more preferred at least 98%, even more preferred at least 99% and most preferred at least 100% identity with the amino acid sequence of SEQ ID NO: 6, or a functional fragment thereof; (b) a polypeptide encoded by a nucleic acid sequence which hybridizes under medium stringency conditions with: (i) nucleotides encoding a mature polypeptide of SEQ ID NO: 6, (ii) a polynucleotide sequence of regions of SEQ ID NO: 5 encoding a mature enzyme, (iii) the cDNA sequence contained in a polynucleotide sequence of regions of SEQ ID NO: 5 encoding a mature enzyme, (iv) a subsequence of (i) or (ii) of at least 100 contiguous nucleotides, or (v) a complementary strand of (i), (ii), (iii) or (iv); and (c) a fragment of (a) or (b) having carbonic anhydrase activity at elevated temperatures. In a preferred embodiment, the polypeptide has an amino acid sequence which differs by eleven amino acids, preferably by nine amino acids, more preferred by seven amino acids, more preferably by five amino acids, even more preferably by three amino acids, and most preferably by one amino acid from the amino acid sequence of SEQ ID NO: 6.

Another particular embodiment of the present invention relates to an isolated polypeptide having carbonic anhydrase activity at elevated temperatures selected from the group consisting of: (a) a polypeptide having an amino acid sequence which has at least 96%, preferably at least 97%, more preferred at least 98%, even more preferred at least 99% and most preferred at least 100% identity with the amino acid sequence of SEQ ID NO: 8, or a functional fragment thereof; (b) a polypeptide encoded by a nucleic acid sequence which hybridizes under medium stringency conditions with: (i) nucleotides encoding a mature polypeptide of SEQ ID NO: 8, (ii) a polynucleotide sequence of regions of SEQ ID NO: 7 encoding a mature enzyme, (iii) the cDNA sequence contained in a polynucleotide sequence of regions of SEQ ID NO: 7 encoding a mature enzyme, (iv) a subsequence of (i) or (ii) of at least 100 contiguous nucleotides, or (v) a complementary strand of (i), (ii), (iii) or (iv); and (c) a fragment of (a) or (b) having carbonic anhydrase activity at elevated temperatures. In a preferred embodiment, the polypeptide has an amino acid sequence which differs by eleven amino acids, preferably by nine amino acids, more preferred by seven amino acids, more preferably by five amino acids, even more preferably by three amino acids, and most preferably by one amino acid from the amino acid sequence of SEQ ID NO: 8.

Another particular embodiment of the present invention relates to an isolated polypeptide having carbonic anhydrase activity at elevated temperatures selected from the group consisting of: (a) a polypeptide having an amino acid sequence which has at least 89%, preferably at least 91%, more preferably at least 94%, more preferred at least 96%, even more preferred at least 98%, even more preferred at least 99% and most preferred at least 100% identity with the amino acid sequence of SEQ ID NO: 10, or a functional fragment thereof; (b) a polypeptide encoded by a nucleic acid sequence which hybridizes under medium stringency conditions with: (i) nucleotides encoding a mature polypeptide of SEQ ID NO: 10, (ii) a polynucleotide sequence of regions of SEQ ID NO: 9 encoding a mature enzyme, (iii) the cDNA sequence contained in a polynucleotide sequence of regions of SEQ ID NO: 9 encoding a mature enzyme, (iv) a subsequence of (i) or (ii) of at least 100 contiguous nucleotides, or (v) a complementary strand of (i), (ii), (iii) or (iv); and (c) a fragment of (a) or (b) having carbonic anhydrase activity at elevated temperatures. In a preferred embodiment, the polypeptide has an amino acid sequence which differs by eleven amino acids, preferably by nine amino acids, more preferred by seven amino acids, more preferably by five amino acids, even more preferably by three amino acids, and most preferably by one amino acid from the amino acid sequence of SEQ ID NO: 10.

Another particular embodiment of the present invention relates to an isolated polypeptide having carbonic anhydrase activity at elevated temperatures selected from the group consisting of: (a) a polypeptide having an amino acid sequence which has at least 97%, preferably at least 97.5%, more preferred at least 98% even more preferred at least 99% and most preferred at least 100% identity with the amino acid sequence of SEQ ID NO: 12, or a functional fragment thereof; (b) a polypeptide encoded by a nucleic acid sequence which hybridizes under medium stringency conditions with: (i) nucleotides encoding a mature polypeptide of SEQ ID NO: 12, (ii) a polynucleotide sequence of regions of SEQ ID NO: 11 encoding a mature enzyme, (iii) the cDNA sequence contained in a polynucleotide sequence of regions of SEQ ID NO: 11 encoding a mature enzyme, (iv) a subsequence of (i) or (ii) of at least 100 contiguous nucleotides, or (v) a complementary strand of (i), (ii), (iii) or (iv); and (c) a fragment of (a) or (b) having carbonic anhydrase activity at elevated temperatures. In a preferred embodiment, the polypeptide has an amino acid sequence which differs by eleven amino acids, preferably by nine amino acids, more preferred by seven amino acids, more preferably by five amino acids, even more preferably by three amino acids, and most preferably by one amino acid from the amino acid sequence of SEQ ID NO: 12.

A polypeptide of the invention is an isolated polypeptide, preferably the preparation of the polypeptide of the invention contains at the most 90% by weight of other polypeptide material with which it may be natively associated (lower percentages of other polypeptide material are preferred, e.g., at the most 80% by weight, at the most 60% by weight, at the most 50% by weight, at the most 40% by weight at the most 30% by weight, at the most 20% by weight, at the most 10% by weight, at the most 9% by weight, at the most 8% by weight, at the most 6% by weight, at the most 5% by weight, at the most 4% by weight at the most 3% by weight, at the most 2% by weight, at the most 1% by weight and at the most 0.5% by weight). Thus, it is preferred that the isolated polypeptide of the invention is substantially pure, preferably the polypeptide is at least 92% pure, i.e., that the polypeptide of the invention constitutes at least 92% by weight of the total polypeptide material present in the preparation, and higher percentages are preferred such as at least 94% pure, at least 95% pure, at least 96% pure, at least 96% pure, at least 97% pure, at least 98% pure, at least 99%, and at the most 99.5% pure. In particular, it is preferred that the polypeptide of the invention is in "essentially pure form, i.e., that the polypeptide preparation is essentially free of other polypeptide material with which it is natively associated. This can be accomplished, for example, by preparing the polypeptide of the invention by means of well-known recombinant methods.

The polypeptide of the invention may be synthetically made, naturally occurring or a combination thereof. In a particular embodiment the polypeptide of the invention may be obtained from a microorganism such as a prokaryotic cell, an archaea cell or a eukaryotic cell, in particular a fungal cell. The cell may further have been modified by genetic engineering.

Polynucleotides

The present invention also relates to polynucleotides, particularly isolated polynucleotides, comprising or consisting of a nucleotide sequence encoding a polypeptide of the invention. In a preferred aspect a nucleotide sequence of the present invention is selected from the group consisting of SEQ ID NO: 1, SEQ ID NO: 3, SEQ ID NO: 5, SEQ ID NO: 7, SEQ ID NO: 9 and SEQ ID NO: 11. In another preferred aspect, the nucleotide sequence is the mature polypeptide coding region of a polynucleotide selected from the group of SEQ ID NO: 1, SEQ ID NO: 3, SEQ ID NO: 5, SEQ ID NO: 7, SEQ ID NO: 9 and SEQ ID NO: 11. The present invention also encompasses nucleotide sequences which encode a polypeptide having an amino acid sequence selected from the group of SEQ ID NO: 2, SEQ ID NO: 4, SEQ ID NO: 6, SEQ ID NO: 8, SEQ ID NO: 10 and SEQ ID NO: 12 or a mature polypeptide thereof, which differ from SEQ ID NO: 1, SEQ ID NO: 3, SEQ ID NO: 5, SEQ ID NO: 7, SEQ ID NO: 9 and SEQ ID NO: 11, respectively, by virtue of the degeneracy of the genetic code. The present invention also relates to subsequences selected from the group of SEQ ID NO: 1, SEQ ID NO: 3, SEQ ID NO: 5, SEQ ID NO: 7, SEQ ID NO: 9 and SEQ ID NO: 11 which encode fragments of SEQ ID NO: 2, SEQ ID NO: 4, SEQ ID NO: 6, SEQ ID NO: 8, SEQ ID NO: 10, and SEQ ID NO: 12, respectively that have carbonic anhydrase activity, preferably at an elevated temperature.

The present invention also relates to mutant polynucleotides comprising at least one mutation in the mature polypeptide coding sequence selected from the group of SEQ ID NO: 1, SEQ ID NO: 3, SEQ ID NO: 5, SEQ ID NO: 7, SEQ ID NO: 9 and SEQ ID NO: 11 in which the mutant nucleotide sequence encodes a polypeptide which consists of amino acids 10 to 237 of SEQ ID NO: 2, SEQ ID NO: 4, SEQ ID NO: 6, SEQ ID NO: 8, SEQ ID NO: 10, or SEQ ID NO: 12, respectively.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from any organism which can be expected to encode a carbonic anhydrase, such organisms may be eukaryotes, including mammals, algae and plants, prokaryotes including bacterial strains of different genera or species as well as archaeon. Preferably, the organisms are thermophilic or hyperthermophilic. Even more preferred the polynucleotide is obtained from a *Bacillus clausii* strain which is not *Bacillus clausii* KSM-K16.

Modification of a nucleotide sequence encoding a polypeptide of the present invention may be necessary for the synthesis of a polypeptide which comprises an amino acid sequence that has at least one substitution, deletion and/or insertion as compared to an amino acid sequence selected from mature polypeptide comprised in SEQ ID NO: 2, SEQ ID NO: 4, SEQ ID NO: 6, SEQ ID NO: 8, SEQ ID NO: 10, or SEQ ID NO: 12.

It will be apparent to those skilled in the art that such modifications can be made to preserve the function of the enzyme i.e., made outside regions critical to the function of the enzyme. Amino acid residues which are essential to the function are therefore preferably not subject to modification, such as substitution. Amino acid residues essential to the function may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for carbonic anhydrase activity to identify amino acid residues that are critical to the activity of the molecule. Sites of substrate-enzyme interaction can be determined by analysis of the three-dimensional structure as determined by such techniques as nuclear magnetic resonance analysis, crystallography or photoaffinity labeling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64). Moreover, a nucleotide sequence encoding an enzyme of the invention may be modified by introduction of nucleotide substitutions which do not give rise to another amino acid sequence of the enzyme encoded by the nucleotide sequence, but which correspond to the codon usage of the host organism intended for production of the enzyme. The introduction of a mutation into the nucleotide sequence to exchange one nucleotide for another nucleotide may be accomplished by site-directed mutagenesis using any of the methods known in the art. Particularly useful is the procedure, which utilizes a super coiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with Dpnl, which is specific for methylated and hemimethylated DNA to digest the parental DNA template and to select for mutation-containing synthesized DNA. Other procedures known in the art may also be used. For a general description of nucleotide substitution, one may consult with, e.g., Ford et al., 1991, *Protein Expression and Purification* 2: 95-107.

The present invention also relates to isolated polynucleotides comprising, preferably consisting of, a nucleotide sequence which encoding a polypeptide of the present invention, which hybridize under very low stringency conditions, preferably low stringency conditions, more preferably medium stringency conditions, more preferably medium-high stringency conditions, even more preferably high stringency conditions, and most preferably very high stringency conditions with a polynucleotide probe selected from the group consisting of:

i) a polynucleotide sequence selected from the group consisting of SEQ ID NO: 1, SEQ ID NO:3, SEQ ID NO: 5, SEQ ID NO: 7, SEQ ID NO: 9 and SEQ ID NO: 11, ii) a cDNA sequence contained in a polynucleotide sequence selected from the group consisting of SEQ ID NO: 1, SEQ ID NO: 3, SEQ ID NO: 5, SEQ ID NO: 7, SEQ ID NO: 9 and SEQ ID NO: 11, or iii) a subsequence of (i) or (ii) encoding a secreted mature polypeptide having the function of the corresponding mature polypeptides comprised in SEQ ID NO: 2, SEQ ID NO: 4, SEQ ID NO: 6, SEQ ID NO: 8, SEQ ID NO: 10 and SEQ ID NO: 12; or iv) a complementary strand of (i), (ii), or (iii) (Sambrook, Fritsch, and Maniatis, 1989, Molecular Cloning, A Laboratory Manual, 2d edition, Cold Spring Harbor, N.Y.).

As will be understood, details and particulars concerning hybridization of the nucleotide sequences will be the same or analogous to the hybridization aspects discussed in the section titled "polypeptides of the invention herein.

The present invention also encompasses a storage medium suitable for use in an electronic, preferably digital, device comprising information of the amino acid sequence of polypeptides of the invention or the nucleotide sequences of the polynucleotide of the invention, in particular any of the polypeptide or polynucleotide sequences of the invention in an electronic or digital form, such as binary code or other digital code. The storage medium may suitably be a magnetic or optical disk and the electronic device a computing device and the information may in particular be stored on the storage medium in a digital form.

Recombinant Expression Vectors.

The present invention also relates to recombinant expression vectors comprising a nucleic acid construct of the invention. Nucleic acid constructs of the invention comprise an isolated polynucleotide of the present invention, preferably operably linked to one or more control sequences which direct the expression of the coding sequence in a suitable host cell under conditions compatible with the control sequences.

Alternatively, a polynucleotide sequence of the present invention or a nucleic acid construct comprising the polynucleotide sequence may be inserted into an appropriate vector for expression. In creating the expression vector, the coding sequence is located in the vector so that the coding sequence is operably linked with the appropriate control sequences for expression. The control sequences may either be provided by the vector or by the nucleic acid construct inserted into the vector.

The control sequence may be an appropriate promoter sequence, a nucleotide sequence which is recognized by a host cell for expression of a polynucleotide encoding a polypeptide of the present invention. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell. Such promoters are well known in the art. The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention, such terminators are well known in the art. The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention, such leader sequences are well known in the art. The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention. The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention. It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art. Further, tags which may aid purification or immobilization of the polypeptide may be added to the polypeptide. Such a tag may for example be a polyhistedine tag (His tag). Preferably, the tag located in the N-terminal or C-terminal of the polypeptide, and may be encoded by the vector. Alternatively, the tag may be located internally in the polypeptide, as long as it does not affect the functionality of the polypeptide.

The recombinant expression vector may be any vector (e.g., a plasmid, phagemid, phage or virus) that can be conveniently subjected to recombinant DNA procedures and can bring about the expression of the nucleotide sequence. The choice of the vector will typically depend on the compatibility of the vector with the host cell into which the vector is to be introduced.

The vectors may be linear or closed circular plasmids. The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome.

The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers that permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers that confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell's genome or autonomous replication of the vector in the cell independent of the genome.

For integration into the host cell genome, the vector may rely on the nucleotide sequence encoding the polypeptide or any other element of the vector for stable integration of the vector into the genome by homologous or nonhomologous recombination. Alternatively, the vector may contain additional nucleotide sequences for directing integration by homologous recombination into the genome of the host cell. The additional nucleotide sequences enable the vector to be integrated into the host cell genome at a precise location(s) in the chromosome(s). To increase the likelihood of integration at a precise location, the integrational elements should preferably contain a sufficient number of nucleotides, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination, or by random integration.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*. Examples of origins of replication for use in a yeast host cell are the 2 micron origin of replication, ARS1, ARS4, the combination of ARS1 and CEN3, and the combination of ARS4 and CEN6. Examples of origins of replication useful in a filamentous fungal cell are AMA1 and ANSI (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883. The origin of replication may be one having a mutation which makes its functioning temperature-sensitive in the host cell (see, e.g., Ehrlich, 1978, *Proceedings of the National Academy of Sciences USA* 75: 1433). The vector may also comprise two or more origins of replication, each origin allowing for replication in a different host cell, e.g., a bacterial origin and yeast origin.

More than one copy of a nucleotide sequence of the present invention may be inserted into the host cell to increase production of the gene product. An increase in the copy number of the nucleotide sequence can be obtained by integrating at least one additional copy of the sequence into the host cell genome or by including an amplifiable selectable marker gene with the nucleotide sequence where cells containing amplified copies of the selectable marker gene, and thereby additional copies of the nucleotide sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Recombinant Host Cells.

The present invention also relates to recombinant a host cell comprising the nucleic acid construct of the invention, which are advantageously used in the recombinant production of the polypeptides. A vector comprising a nucleotide sequence of the present invention is introduced into a host cell so that the vector is maintained as a chromosomal integrant or as a self-replicating extra-chromosomal vector as described earlier.

The host cell may be a prokaryote such as bacterial cells, an archaea or an eukaryote such as fungal cells, plant cells, insect cells, or mammalian cells.

Useful prokaryotes are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus halodurans, Bacillus lautus, Bacillus lentus, Bacillus licheniformis, Bacillus megaterium, Bacillus stearothermophilus, Bacillus subtilis,* and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus, Bacillus licheniformis, Bacillus stearothermophilus,* or *Bacillus subtilis* cell. In another preferred embodiment, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, Journal of Bacteriology 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

In a preferred embodiment, the host cell is a fungal cell. "Fungi as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., In, *Ainsworth and Bisby's Dictionary of The Fungi*, 8th edition, 1995, CAB International, University Press, Cambridge, UK, page 171) and all mitosporic fungi (Hawksworth et al., In, *Ainsworth and Bisby's Dictionary of The Fungi*, 8th edition, 1995, CAB International, University Press, Cambridge, UK). In a more preferred embodiment, the fungal host cell is a yeast cell. "Yeast as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, eds, *Soc. App. Bacteriol. Symposium Series No. 9*, 1980).

In an even more preferred embodiment, the yeast host cell is a *Candida, Hansenula, Kluyveromyces, Pichia, Saccharomyces, Schizosaccharomyces,* or *Yarrowia* cell. In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi include all filamentous forms of the subdivision Eumycota and Oomycota (as defined by Hawksworth et al., In, *Ainsworth and Bisby's Dictionary of The Fungi*, 8th edition, 1995, CAB International, University Press, Cambridge, UK). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative. In an even more preferred embodiment, the filamentous fungal host cell is a cell of a species of, but not limited to, *Acremonium, Aspergillus, Fusarium, Humicola, Mucor, Myceliophthora, Neurospora, Penicillium, Thielavia, Tolypocladium,* or *Trichoderma*. In a most preferred embodiment, the filamentous fungal host cell is an *Aspergillus awamori*, *Aspergillus foetidus*, *Aspergillus japonicus*, *Aspergillus nidulans*, *Aspergillus niger* or *Aspergillus oryzae* cell. In another most preferred embodiment, the filamentous fungal host cell is a *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens*, *Humicola lanuginosa*, *Mucor miehei*, *Myceliophthora thermophila*, *Neurospora crassa*, *Penicillium purpurogenum*, *Thielavia terrestris*, *Trichoderma harzianum*, *Trichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156 and WO 96/00787. Yeast may be transformed using the procedures described by Becker and Guarente, In Abelson and Simon, editors, Guide to Yeast Genetics and Molecular Biology, *Methods in Enzymology* 194: 182-187, Academic Press, Inc., New York; Ito et al., 1983, *Journal of Bacteriology* 153: 163; and Hinnen et al., 1978, *Proceedings of the National Academy of Sciences USA* 75: 1920.

A particular embodiment of the present invention is a recombinant host cell transformed with a polynucleotide selected from the group consisting of SEQ ID NO: 1, SEQ ID NO: 3, SEQ ID NO: 5, SEQ ID NO: 7, SEQ ID NO: 9, SEQ ID NO: 11 SEQ ID NO: 13 and SEQ ID NO: 15. Preferably, such a host cell does not contain an inherent carbonic anhydrase encoding gene, or such a gene has been disrupted. Thereby the recombinant carbonic anhydrase is the only carbonic anhydrase produced by a recombinant host cell of the present invention.

Methods for Preparing Carbonic Anhydrase

The present invention also relates to methods for producing a carbonic anhydrase enzyme of the invention comprising (a) cultivating a host cell comprising a nucleotide sequence encoding a carbonic anhydrase which strain is capable of expressing and secreting the carbonic anhydrase and (b) recovering the carbonic anhydrase. In a particular embodiment the host cell is a wild type *Bacillus clausii* strain, which inherently contain a carbonic anhydrase encoding gene. More preferred the wild type strain is the *Bacillus clausii* strain deposited as NCIB 10309. In another embodiment the host cell is a recombinant host cell as described above.

In these methods of the invention, the cells are cultivated in a nutrient medium suitable for production of the enzyme using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). As the enzyme is secreted into the nutrient medium, the enzyme can be recovered directly from the medium. If the enzyme is not secreted, it can be recovered from cell lysates.

The enzyme may be detected using methods known in the art that are specific for the polypeptides. These detection methods may include use of specific antibodies, formation of an enzyme product, or disappearance of an enzyme substrate. For example, an enzyme assay may be used to determine the carbonic anhydrase activity, e.g., the method described by (Wilbur, 1948, *J. Biol. Chem.* 176: 147-154). The set up is based on the pH change of the assay mixture due to the formation of bicarbonate from carbon dioxide as given in equation 1: $[CO_2+H_2O \leftrightarrows HCO_3^- + H^+]$. A particular way of performing this activity assay is described in (Chirica et al., 2001, *Biochim. Biophys. Acta* 1544: 55-63). Further, the kinetics of the carbonic anhydrase may be assessed by its capability of cleaving para-nitrophenol-acetate to nitrophenol and acetate.

The enzyme of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989).

Compositions Comprising Polypeptides and Methods for their Preparation

The invention provides a composition comprising a carbonic anhydrase of the present invention and preferably an excipient and a method for preparing such a composition comprising admixing the polypeptide of the invention with an excipient.

In a particular embodiment the carbonic anhydrase of the invention is the major (polypeptide) component of the composition, e.g., a mono-component composition. The excipient in this context is to be understood as any auxilliary agent or compound used to formulate the composition and includes solvent (e.g., water, inorganic salts, fillers, pigments, waxes), carriers, stabilizers, cross-linking agents, adhesives, preservatives, buffers and the like.

The composition may further comprise one or more additional enzymes, such as an aminopeptidase, amylase, carbohydrase, carboxypeptidase, catalase, cellulase, chitinase, cutinase, cyclodextrin glycosyltransferase, decarboxylase, deoxyribonuclease, esterase, alpha-galactosidase, beta-galactosidase, glucoamylase, alpha-glucosidase, beta-glucosidase, haloperoxidase, invertase, laccase, lipase, mannosidase, monooxygenase, nitrilase, oxidase, pectinolytic enzyme, peptidoglutaminase, peroxidase, phytase, polyphenoloxidase, proteolytic enzyme, ribonuclease, transglutaminase, or xylanase.

The compositions may be prepared in accordance with methods known in the art and may be in the form of a liquid or a solid composition. For instance, the enzyme composition may be formulated using methods known to the art of formulating technical enzymes and/or pharmaceutical products, e.g., into coated or uncoated granules or micro-granules. The polypeptide of the invention may thus be provided in the form of a granule, preferably a non-dusting granule, a liquid, in particular a stabilized liquid, a slurry or a protected polypeptide.

For certain applications, immobilization of the polypeptide may be preferred. An immobilized enzyme comprises two essential functions, namely the non-catalytic functions that are designed to aid separation (e.g., isolation of catalysts from the application environment, reuse of the catalysts and control of the process) and the catalytic functions that are designed to convert the target compounds (or substrates) within the time and space desired (Cao, Carrier-bound Immobilized Enzymes: Principles, Applications and Design, Wiley-VCH Verlag GmbH & Co. KGaA, Weinheim, Germany, 2005). When an enzyme is immobilized it is made insoluble to the target compounds (e.g., substrates) it aids converting and to the solvents used. An immobilized enzyme product can be separated from the application environment in order to facilitate its reuse, or to reduce the amount of enzyme needed, or to use the enzyme in a process where substrate is continuously delivered and product is continuously removed from proximity to the enzyme, which, e.g., reduces enzyme cost. Furthermore, enzymes are often stabilized by immobilization. A process involving immobilized enzymes is often continuous, which facilitates easy process control. The immobilized enzyme can be retained as a heterogeneous catalyst by mechanical means, or by inclusion in a definite space. The latter can be done by microencapsulation, e.g., in semi permeable membranes or by inclusion in UF systems using, e.g., hollow fiber modules, etc. Immobilization on porous carriers is also commonly used. This includes binding of the enzyme to the carrier, e.g., by adsorption, complex/ionic/covalent binding, or just simple absorption of soluble enzyme on the carrier and subsequent removal of solvent. Cross-linking of the enzyme can also be used as a means of immobilization. Immobilization of enzyme by inclusion into a carrier is also industrially applied. (Buchholz et al., Biocatalysts and Enzyme Technology, Wiley-VCH Verlag GmbH & Co. KGaA, Weinheim, Germany, 2005). Specific methods of immobilizing enzymes such as carbonic anhydrase include, but are not limited to, spraying of the enzyme together with a liquid medium comprising a polyfunctional amine and a liquid medium comprising a cross-linking agent onto a particulate porous carrier as described in WO 2007/036235 (hereby incorporated by reference), linking of carbonic anhydrase with a cross-linking agent (e.g., glutaraldehyde) to an ovalbumin layer which in turn adhere to an adhesive layer on a polymeric support as described in WO 2005/114417 (hereby incorporated by reference), or coupling of carbonic anhydrase to a silica carrier as described in U.S. Pat. No. 5,776,741 or to a silane, or a CNBr activated carrier surface such as glass, or co-polymerization of carbonic anhydrase with methacrylate on polymer beads as described in Bhattacharya et al., 2003, *Biotechnol. Appl. Biochem.* 38: 111-117 (hereby incorporated by reference). In an embodiment of the present invention carbonic anhydrase is immobilized on a matrix. The matrix may for example be selected from the group beads, fabrics, fibers, hollow fibers, membranes, particulates, porous surfaces, rods, structured packing, and tubes. Specific examples of suitable matrices include alumina, bentonite, biopolymers, calcium carbonate, calcium phosphate gel, carbon, cellulose, ceramic supports, clay, collagen, glass, hydroxyapatite, ion-exchange resins, kaolin, nylon, phenolic polymers, polyaminostyrene, polyacrylamide, polypropylene, polymerhydrogels, sephadex, sepharose, silica gel, precipitated silica, and TEFLON-brand PTFE. In an embodiment of the present invention carbonic anhydrase is immobilized on a nylon matrix according to the techniques described in Methods in Enzymology volume XLIV (section in the chapter: Immobilized Enzymes, pages 118-134, edited by Klaus Mosbach, Academic Press, New York, 1976), hereby incorporated by reference.

The polypeptide to be included in the composition may be stabilized in accordance with methods known in the art e.g., by stabilizing the polypeptide in the composition by adding and antioxidant or reducing agent to limit oxidation of the polypeptide or it may be stabilized by adding polymers such as PVP, PVA, PEG, sugars, oligomers, polysaccharides or other suitable polymers known to be beneficial to the stability of polypeptides in solid or liquid compositions. A preservative, such as Proxel, can be added to extend shelf life or performance in application.

In a further embodiment the composition of the invention is a composition applicable in the capture of carbon dioxide.

EXAMPLES

Example 1

Cloning and Expression of *B. clausii* Carbonic Anhydrase in *B. subtilis*

Carbonic anhydrase sequences were identified by PCR screening on genomic DNA from different *Bacillus clausii* strains. Genomic DNA from the *B. clausii* strains was prepared by using the Qiagen Blood DNA kit following the manufacturer's protocol.

PCR Screening

PCR (1) was performed in a total volume of 50 microliters, the following reagents were added, 1 microliter of genomic DNA preparation (template), 10 pmol of each of the primers (Bcaf1 and Bcar1), dNTPs and Expand polymerase in buffer #1 (Roche). The PCR conditions were 94° C. for 2 min; 9 cycles of 94° C. for 15 sec; 55° C. for 45 sec; 68° C. for 1 min; followed by 68° C. for 10 min; 4° C. for 20 min and 15° C. until the end of the PCR program.

The primers used for the PCR screening were:

Bcaf1 gcttctgctgctagtttcctgtca (SEQ ID NO: 19)

Bcar1 ataatgaaaaccgatttctctgtcgc (SEQ ID NO: 20)

Obtained PCR products (SEQ ID NOs: 1, 3, 5, 7, 9, 11 and 13) had the length of approx. 700 bp, were size-excluded and sequenced with the same primers. The amino acid translations of the PCR products from PCR(1) represent SEQ ID NOs: 2, 4, 6, 8, 10, 12 and 14. The mature native enzymes start at position 1 of SEQ ID NOs: 2, 4, 6, 8, 10, 12 and 14. Table 1 below indicates the identity at the polypeptide level between the native enzymes translated from the PCR products.

TABLE 1

Identity matrix

| | SEQ ID NO: 10 | SEQ ID NO: 6 | SEQ ID NO: 2 | SEQ ID NO: 4 | SEQ ID NO: 14 | SEQ ID NO: 12 | SEQ ID NO: 8 |
|---|---|---|---|---|---|---|---|
| SEQ ID NO: 10 | 100 | 97 | 91 | 92 | 89 | 91 | 90 |
| SEQ ID NO: 6 | | 100 | 92 | 93 | 91 | 93 | 92 |
| SEQ ID NO: 2 | | | 100 | 99 | 94 | 96 | 95 |
| SEQ ID NO: 4 | | | | 100 | 94 | 96 | 96 |
| SEQ ID NO: 14 | | | | | 100 | 97 | 96 |

TABLE 1-continued

Identity matrix

|  | SEQ ID NO: 10 | SEQ ID NO: 6 | SEQ ID NO: 2 | SEQ ID NO: 4 | SEQ ID NO: 14 | SEQ ID NO: 12 | SEQ ID NO: 8 |
|---|---|---|---|---|---|---|---|
| SEQ ID NO: 12 |  |  |  |  |  | 100 | 100 |
| SEQ ID NO: 8 |  |  |  |  |  | 100 | 100 |

Generation of PCR Fragment for SOE PCR

PCR (2) was performed with the same parameters as in PCR(1), except that primers and template were replaced with 10 pmol of each of the primers blcaTSP and bcl1362rev and 1 ul of purified product from PCR(1) (SEQ 1, 7, 9, 11 and 13).

bclaTSP: cttgctgcctcattctgcagccgcgttgaaagcatcatggtc (SEQ ID NO: 21)

bcl1362rev: tccgatcccctttccattctactttaatgataatgaaaaccga (SEQ ID NO: 22)

The PCR products had an approximate length of 700 by and the PCR products were purified. The PCR products were suitable for a subsequent SOE PCR fusion reaction (see PCR (3)). Due to the nature of primer bclaTSP the translated amino acid sequence of this PCR (2) product was changed to LLPHSAAALKASW . . . , where LLPHSAAA represents a fragment of the amyL gene (see SOE fusion reaction below) and LKASW represents the N-terminal of the truncated mature peptide obtained by recombinant expression of the CAs. Hence, the mature recombinant peptide of all the cloned CAs start at position 10 in SEQ ID NOs: 2, 8, 10, 12 and 14 and has the N-terminal amino acid sequence LKASW with a leucine as the most N-terminal amino acid, irrespective of the amino acid indicated in that position of the respective sequence.

SOE Fusion

In PCR(3) the signal peptide from the alpha-amylase from *B. licheniformis* (AmyL) was fused by SOE fusion as described in WO 99/43835 (hereby incorporated by reference) in frame to the DNA encoding the carbonic anhydrase that was obtained in PCR (2). The nucleotide fragments obtained from PCR(3) containing the carbonic anhydrase coding sequence were integrated by homologous recombination into the *Bacillus subtilis* host cell genome. The gene construct was expressed under the control of a triple promoter system (as described in WO 99/43835). The gene coding for chloramphenicol acetyl-transferase was used as maker (as described in Diderichsen et al., 1993, *Plasmid* 30: 312-315).

Chloramphenicol resistant transformants were analyzed by DNA sequencing to verify the correct DNA sequence of the construct. One expression clone for each recombinant sequence was selected, (SEQ ID NOs: 2, 8, 10, 12 and 14 starting at position 10 with LKASW).

The individual carbonic anhydrase expression clones were fermented on a rotary shaking table in 1 L baffled Erlenmeyer flasks each containing 400 ml soy based media supplemented with 34 mg/l chloramphenicol. The clones were fermented for 4 days at 37° C. The carbonic anhydrase activity in the culture broth was determined according to Wilbur, 1948, *J. Biol. Chem.* 176: 147-154 (see Example 4). Alternatively, the carbonic anhydrase activity was measured as esterase activity with para-nitrophenolacetate as substrate according to Chirica et al., 2001, *Biochim. Biophys. Acta* 1544(1-2): 55-63 (see Example 5).

Example 2

Cloning of CA from *B. halodurans*

The CA from *B. halodurans* (SEQ ID NO: 16) was cloned according to Example 1 with the following modifications. No screening was performed. Instead, the genomic DNA of strain *B. halodurans* C-125 (JCM9153) was used as template and primers for PCR(2) were cahTSP ctgcctcattctgcagccgcgccttccacagaaccagtcgat (SEQ ID NO: 23)

cahrev: tccgatcccctttccattctactctattcagtgatcacgtcat (SEQ ID NO: 24).

Due to the nature of primer cahTSP the translated amino acid sequence of this PCR (2) product was changed to LPHSAAAPSTEPVD . . . , where LPHSAAA represents a fragment of the amyL gene (see SOE fusion reaction below) and PSTEPVD represents the N-terminal of the mature peptide obtained by recombinant expression of the CAs. The final SOE PCR was done according to Example 1.

Example 3

Enzyme Purification

Six recombinant carbonic anhydrases (SEQ ID NOs: 2, 8, 10, 12, and 14 (cloned as described in Example 1 and SEQ ID NO: 16 cloned as described in Example 2) were purified by the same identical procedure: The culture broth was centrifuged (26.000×g, 20 min) and the supernatant was filtered through a Whatman 0.45 micro-m filter. The 0.45 micro-m filtrate was approx. pH 7 and conductivity was approx. 20 mS/cm. The 0.45 micro-m filtrate was transferred to 10 mM HEPES/NaOH, pH 7.0 by G25 sephadex chromatography and applied to a 100 ml Q-sepharose FF column equilibrated in 10 mM HEPES/NaOH, pH 7.0. After washing the column with the equilibration buffer, bound protein was eluted with a linear NaCl gradient (0→0.5 M) over 3 column volumes. Fractions were collected during elution and these fractions were tested for carbonic anhydrase activity (see Example 4). Two peaks with CA activity were identified. N-terminal sequencing revealed that the first elution peak contained a superoxide dismutase and the second elution peak (peak B) contained carbonic anhydrase. Peak B was diluted 7× with deionized water and applied to a 40 ml SOURCE 30Q column equilibrated in 10 mM HEPES/NaOH, pH 7.0. The column was washed with equilibration buffer and eluted with a linear NaCl gradient (0→0.5 M). Elution fractions from the column were analyzed for CA activity and the positive fractions were analyzed by SDS-PAGE. Fractions which revealed a predominant band on a coomassie stained SDS-PAGE gel were pooled into a carbonic anhydrase batch. The enzyme purity of CAs corresponding to SEQ ID NOs: 2, 8, 10 and 12 was estimated to be 80% pure, and the enzyme corresponding to SEQ ID NOs: 14 and 16 was above 95% pure.

Example 4

Detection of Carbonic Anhydrase Activity

The test for the detection of carbonic anhydrase was described by Wilbur, 1948, *J. Biol. Chem.* 176: 147-154. The set up is based on the pH change of the assay mixture due to the formation of bicarbonate from carbon dioxide as given in equation 1: $[CO_2 + H_2O \rightarrow HCO_3^- + H^+]$.

The activity assay used in this study was derived from the procedure of Chirica et al., 2001, *Biochim. Biophys. Acta* 1544(1-2): 55-63. A solution containing approximately 60 to 70 mM $CO_2$ was prepared by bubbling $CO_2$ into 100 ml distilled water using the tip of a syringe approximately 45 min to 1 h prior to the assay. The $CO_2$ solution was chilled in an ice-water bath. To test for the presence of carbonic anhydrase, 2 ml of 25 mM Tris, pH 8.3 (containing sufficient bromothymol blue to give a distinct and visible blue color) were added to two 13×100 mm test tubes chilled in an ice bath. To one tube, 10 to 50 microliters of the enzyme containing solution (e.g., culture broth or purified enzyme) was added, and an equivalent amount of buffer was added to the second tube to serve as a control. Using a 2 ml syringe and a long cannula, 2 ml of $CO_2$ solution was added very quickly and smoothly to the bottom of each tube. Simultaneously with the addition of the $CO_2$ solution, a stopwatch was started. The time required for the solution to change from blue to yellow was recorded (transition point of bromothymol blue is pH 6-7.6). The production of hydrogen ions during the $CO_2$ hydration reaction lowers the pH of the solution until the color transition point of the bromothymol blue is reached. The time required for the color change is inversely related to the quantity of carbonic anhydrase present in the sample. The tubes must remain immersed in the ice bath for the duration of the assay for results to be reproducible. Typically, the uncatalyzed reaction (the control) takes approximately 2 min for the color change to occur, whereas the enzyme catalyzed reaction is complete in 5 to 15 s, depending upon the amount of enzyme added. Detecting the color change is somewhat subjective but the error for triple measurements was in the range of 0 to 1 sec difference for the catalyzed reaction. One unit is defined after Wilbur [1 U=$(1/t_c)-(1/t_u) \times 1000$] where U is units and $t_c$ and $t_u$ represent the time in seconds for the catalyzed and uncatalyzed reaction, respectively (Wilbur, 1948, *J. Biol. Chem.* 176: 147-154). These units are also termed Wilbur-Anderson units (WAU).

Example 5

Kinetic Assay for Carbonic Anhydrase Activity with p-Nitrophenyl Acetate

Twenty microliters purified CA enzyme sample obtained as described in Example 3 (diluted in 0.01% Triton X-100) was placed in the bottom of a micro-titer plate (MTP) well. The assay was started at room temperature by adding 200 microliters para-nitrophenol-acetate ((pNp-acetate, Sigma, N-8130) substrate solution in the MTP well. The substrate solution was prepared immediately before the assay by mixing 100 microliters pNP-acetate stock solution (50 mg/ml pNP-acetate in DMSO. Stored frozen) with 4500 microliters assay buffer (0.1 M Tris/HCl, pH 8.0). The increase in $OD_{405}$ was monitored. In the assay a buffer blind (20 microliters assay buffer instead of CA sample) was included. The difference in $OD_{405}$ increase between the sample and the buffer blind was a measure of the carbonic anhydrase activity (CA activity=$\Delta OD_{405}$(sample)–$OD_{405}$(buffer)).

Example 6

Temperature Stability Assay

The purified CA enzyme (SEQ ID NOs: 2, 8, 10, 12, 14 and 16 obtained as described in Example 3) was diluted 10× in 50 mM HEPES/NaOH, pH 7.5 and aliquots were incubated for 15 minutes at different temperatures (15 to 80° C.). CA enzyme of SEQ ID NO: 14 was additionally incubated for 2 hours at different temperatures. After incubation, residual activity was measured as described in Example 5. The result of the temperature stability assay is shown in Table 2. Clearly, CAs from *M. thermophila*, *B. halodurans* and *B. clausii* showed higher thermostability than Human CAII. Further, *B. clausii* CA was superior in terms of thermostability over the *M. thermophila* CA. The data for Human CAII and *M. thermophila* were taken from Alber and Ferry, 1996, *J. Bacteriol.* 178: 3270-3274.

TABLE 2

Temperature stability of different carbonic anhydrases

| Residual activity [%] | Temperature °C. | | | | | | | | |
|---|---|---|---|---|---|---|---|---|---|
| CA | 15 | 25 | 37 | 50 | 55 | 60 | 65 | 70 | 75 | 80 |
| Data from Alber & Ferry, 1996, J. Bacteriol. 178 3270-3274 | | | | | | | | | |
| Human CAII | — | — | 95 | 78 | 35 | 5 | 0 | 0 | 0 | 0 |
| *M. thermophila* | — | — | — | — | 95 | 90 | 80 | 32 | 5 | 0 |
| Incubation time 15 min | | | | | | | | | |
| *B. halodurans* (SEQ ID NO 16) | 93 | 101 | 105 | 61 | n.d. | 15 | n.d. | 11 | n.d. | 8 |
| *B. clausii* (SEQ ID NO 14) | 92 | 104 | 104 | 107 | n.d. | 94 | n.d. | 49 | n.d. | 43 |
| *B. clausii* (SEQ ID NO 2) | 99 | 95 | 106 | 104 | n.d. | 90 | n.d. | 9 | n.d. | 14 |
| *B. clausii* (SEQ ID NO 8) | 98 | 99 | 102 | 99 | n.d. | 93 | n.d. | 67 | n.d. | 49 |
| *B. clausii* (SEQ ID NO 10) | 101 | 98 | 101 | 89 | n.d. | 64 | n.d. | 20 | n.d. | 28 |
| *B. clausii* (SEQ ID NO 12) | 97 | 101 | 105 | 95 | n.d. | 89 | n.d. | 63 | n.d. | 54 |
| Incubation time 2 hours | | | | | | | | | |
| *B. clausii* (SEQ ID NO 14) | 96 | 100 | 105 | 96 | n.d. | 50 | n.d. | 37 | n.d. | 30 | n.d. = not determined

Differential Scanning Calorimetry (DSC)

The purified CA enzyme (SEQ ID NO: 14 and SEQ ID NO: 16 obtained as described in Example 3) was diluted to approx. 1 mg/ml in 50 mM HEPES/NaOH, pH 7.5. DSC was performed with a 90° C./hour scan rate and 20° C. to 90° C. scan range. The melting point of *B. clausii* (SEQ ID NO: 14) and *B. halodurans* (SEQ ID NO: 16) CA was 67.4° C. and 63.1° C., respectively.

Example 7

Amino Terminal Protein Sequencing

Purified recombinant CAs (SEQ ID NOs: 2, 8, 10, 12, 14 and 16 obtained as described in Example 3) were sequenced by Edman sequencing. The determined sequences are shown in Table 3. All sequences match the predicted mature peptide sequence, except for the CA from *B. halodurans* (SEQ ID NO: 16) where a truncated enzyme starting at position 18 in SEQ ID NO: 16 was obtained after purification. The protein molecular weight of the recombinant CAs was determined by Electrospray Ionization Time-Of-Flight Mass Spectrometry (ES-TOF MS).

TABLE 3

N-terminal sequences of recombinant CAs.

| SEQ ID NO | Protein Sequence (Edman) | Molecular weight by MS |
|---|---|---|
| 2 | LKASWSYEGE (SEQ ID NO: 25) | 25551 Da |
| 8 | LKASWSYEGD (SEQ ID NO: 26) | 25522 Da |
| 10 | LKASWSYEGE (SEQ ID NO: 27) | 25286 Da |
| 12 | LKASWSYEGD (SEQ ID NO: 28) | 25566 Da |
| 14 | LKASWSYE (SEQ ID NO: 29) | 25628 Da |
| 16 | GGAHEVHWSY (SEQ ID NO: 30) | 26143 Da |

Example 8

Thermal Stability Using Wilbur-Anderson Assay

The thermal stability of purified CA enzymes corresponding to SEQ ID NOs: 2, 8, 10, 12 and 14 and Bovine carbonic anhydrase (Sigma, catalog nr. C3934) was measured. The CA's were obtained as described in Example 3.

The thermal stability was measured as follows: 10 microliters of each enzyme was diluted 10 folds in 1 M $NaHCO_3$ Solution (pH=8.05) and was incubated for 15 minutes or 2 hours at desired temperature. 1 M $NaHCO_3$ solutions were also heated at the same temperature as control. Solutions were cooled down to room temperature before conducting the assay. The Wilbur-Anderson activity of the heated enzyme solutions was measured according to the procedure of Example 4 with the following minor changes. The $CO_2$ solution was prepared 30 min prior to the assay, the ice bath was substituted with a water bath of 4° C., the amount of enzyme was 10 microliters and the uncatalyzed reaction (the control) takes approximately 40 to 50 seconds. The residual activity after incubation at elevated temperatures is presented in Table 4.

TABLE 4

Temperature stability of different carbonic anhydrases

| Residual activity [%] | Temperature [° C.] | | | | | |
|---|---|---|---|---|---|---|
| CA | 25 | 37 | 50 | 60 | 70 | 80 |
| Incubation time 15 min | | | | | | |
| B. clausii (SEQ ID NO 2) | 100 | 125.7 | 121.5 | 117.6 | 35.3 | 5.4 |
| B. clausii (SEQ ID NO 8) | 100 | 106 | 112.3 | 109.5 | 110 | 16.9 |
| B. clausii (SEQ ID NO 10) | 100 | 89.7 | 89.7 | 86.3 | 38.0 | 14.2 |
| B. clausii (SEQ ID NO 12) | 100 | 115.1 | 125.2 | 139.6 | 25.7 | n.d. |
| B. clausii (SEQ ID NO 14) | 100 | 119.5 | 99.4 | 84.9 | 47.2 | 6.8 |
| Bovine CA | 100 | 100 | 93.7 | 4.4 | 1.1 | |
| Incubation time 2 h | | | | | | |
| B. clausii (SEQ ID NO 8) | n.d. | n.d. | n.d. | n.d. | 43.3 | n.d. | n.d. = not determined

Example 9

Extraction of $CO_2$ from a Mixed Gas Stream in a Hollow Fiber Bioreactor

A lab-scale hollow fiber contained liquid membrane bioreactor (HFB) was set up to selectively capture $CO_2$ from a gas stream which could resemble a flue gas.

Hollow Fiber Membrane Bioreactor Set-up

Porous hydrophobic hollow fiber membranes provide a high surface area of contact between the gas stream and membrane liquid. As a result they facilitate carbonation of a liquid or removal of $CO_2$ from a liquid. The selected module consists of 2300 parallel hollow fibers with 0.18 $m^2$ active surface area and average pore size of 0.01×0.04 micro-m ((Liqui-cel® MiniModule® 1×5.5 purchased from Membrana, North Carolina, USA). These membranes are easy to scale-up to industrial scale and have been used in industry for wastewater treatment and beverage carbonation. A schematic drawing of the bioreactor set-up is shown in FIG. 1. In the set-up membrane liquid was passed through the hollow fibers lumen using a positive displacement pump. The liquid flow rate was set to about 2 ml/min. The gas stream containing a mixture of 15% $CO_2$ (9 Cubic Centimeters per Minute (CCM)) and 85% $N_2$ (51 CCM) (feed gas) entered the feed side of the hollow fibers counter-currently and the treated gas stream (scrubbed gas) exited the module at the sweep side of the hollow fibers. Two mass flow controllers were used to mix nitrogen and carbon dioxide with consistent concentration through out the experiments. A mass flow meter was used to monitor the flow of the scrubbed gas and the feed gas as they exit the reactor. The gas and liquid flows and pressures were adjusted to avoid entering liquid to the gas phase and gas bubbles in the liquid phase of the module.

The purpose of this set-up was the hydration of $CO_2$ to bicarbonate which was measured by analyzing the $CO_2$ concentration in feed gas and scrubbed gas using a gas chromatograph (GC).

Gas Chromatography Method (GC-TCD)

A Shimadzu 2010 gas chromatograph with a thermal conductivity detector and a gas sampling valve was used for $CO_2$ concentration measurement. A capillary Carboxen Plot 1010 column was used to detect nitrogen and carbon dioxide. The column was heated isothermally for 7 minutes at 35° C., the temperature was increased with 20° C./min rate to 200° C. and it was maintained at 200° C. for 2 minutes. Injector and detector temperatures were maintained at 230° C. Column flow is 1 ml/min, split ratio 10 to 1 and carrier gas was helium. Nitrogen and carbon dioxide peaks were detected at retention times 6.4 and 15.3 minutes, respectively. The $CO_2$ peak was calibrated using three carbon dioxide standards with 1000 ppm, 1% and 10% $CO_2$ in nitrogen purchased from Scott Specialty gases (Pennsylvania, USA).

Membrane Liquid

Initially 1 M Sodium bicarbonate pH=8 was selected as membrane liquid. However, it was found that the sodium bicarbonate solution was saturated with $CO_2$ at this pH, as a result it was not a very suitable membrane liquid for the hydration reaction (carbonation). A 1 M sodium bicarbonate solution with a pH of 9 or above was more suitable for $CO_2$ hydration, since it was not saturated with carbon dioxide/bicarbonate. A 1 M sodium bicarbonate solution, pH 9.0 was used as a control solution without enzyme. In another experiment after rinsing the hollow fiber module with de-ionized (DI) water, a solution of 8 parts 1 M sodium bicarbonate pH 9.6+2 parts carbonic anhydrase of SEQ ID NO: 14, corresponding to a final CA concentration of 0.6 g pure enzyme protein/L, was used as membrane liquid. The $CO_2$ concentration in the feed gas and scrubbed gas using these membrane liquids was analyzed by GC. Each experiment was at least repeated three times using different modules and at least three injections to GC were made.

Results

Table 5 shows the data collected using each membrane liquid. It was found that the carbon dioxide concentration in the scrubbed gas exiting the HFCLMB is highly dependent on the pH of the sodium bicarbonate control solution in the membrane liquid. An increase in the pH of the bicarbonate solution increases the rate of the hydration of carbon dioxide to bicarbonate.

Furthermore, it was found that when carbonic anhydrase of SEQ ID NO: 14 was added to the sodium bicarbonate solution at room temperature, the amount of $CO_2$ in the scrubbed gas was significantly reduced and the selectivity of the reactor for $CO_2$ has been increased substantially. An enzyme-bicarbonate solution with pH 9.95 was also tested as the membrane liquid and no $CO_2$ peak was detected in the scrubbed gas. In other words, at pH 9.95 nearly complete removal of $CO_2$ from feed gas was observed.

TABLE 5

Effect of membrane liquid on the $CO_2$ concentration of the gas stream exiting the hollow fiber membrane bioreactor

| Membrane liquid | % CO2 in Scrubbed gas (avg.) | % CO2 in feed gas (avg.) | % CO2 removed (avg.) |
|---|---|---|---|
| DI Water | 13.6 | 14.2 | 4.8 |
| 1 M NaHCO$_3$ pH 9.0 | 11.6 | 15.0 | 22.7 |
| 1 M NaHCO$_3$ pH 9.5 | 10.2 | 15.3 | 33.1 |
| 0.6 g/L CA in 1 M NaHCO$_3$ pH 9.5 | 0.85 | 14.3 | 94.1 |
| 0.6 g/L CA in 1 M NaHCO$_3$ pH 9.95 | <0.1 | 15.3 | >99 |

These results indicate that carbonic anhydrase of SEQ ID NO: 14 even in low dose (~0.6 g enzyme protein/L) significantly increases the efficiency of the hollow fiber membrane reactor when compared to the control.

Example 10

Extraction of $CO_2$ from a Mixed Gas Stream in a Hollow Fiber CLM Bioreactor

A lab-scale hollow fiber contained liquid membrane bioreactor (HFB) was set up to selectively capture $CO_2$ from a gas stream which could resemble a biogas composition.

The bioreactor set-up was essentially the same as described in Example 9. Except that the gas stream contained a mixture of 40% $CO_2$ (8 CCM) and 60% $CH_4$ (12 CCM) which entered the feed side of the hollow fibers. The gas which exits the hollow fiber membrane is termed the enriched gas, since the purpose of this set-up is to show that the percentage of methane in a biogas stream can be increased using a carbonic anhydrase containing bioreactor which captures $CO_2$ from the produced gas stream. This is possible by selective hydration of $CO_2$ component of the gas mix to bicarbonate ions in liquid phase. The efficiency of this after-treatment was measured by analyzing the methane concentration in feed gas and enriched gas using a gas chromatograph (GC).

Gas Chromatography Method (GC-FID)

A Shimadzu 2010 gas chromatograph with flame ionization detector and a gas sampling valve was used for $CH_4$ concentration measurement. A capillary Carboxen Plot 1010 column was used to detect methane. The column was heated isothermally for 3.5 minutes at 200° C. Injector and detector temperatures were maintained at 230° C. Column flow was 2.35 ml/min, split ratio 20 to 1 and carrier gas was helium. Hydrogen and air flow were 45 and 450 mL/min, respectively. The methane peak was detected at retention time 1.9 minutes. The $CH_4$ peak was calibrated using four methane standards with 1000 ppm, 1%, 10% and 99% methane in nitrogen purchased from Scott Specialty gases.

Membrane Liquid

The membrane liquid used was a 1 M Sodium bicarbonate solution at pH 9.3 for the control. The carbonic anhydrase enzyme and concentration were as described in Example 9.

Results

Table 6 shows the data collected using $CO_2$—$CH_4$ mixtures. From this it can be seen that at room temperature, the amount of $CO_2$ removed from the gas stream was increased substantially when a carbonic anhydrase was added to the membrane liquid. Therefore, the amount of $CO_2$ captured in the bioreactor was significantly increased and as a result, the methane content in the exit gas stream was significantly increased.

TABLE 6

Effect of membrane liquid on the methane concentration of the biogas stream exiting the hollow fiber membrane bioreactor

| Membrane liquid | % CH$_4$ in Enriched stream (avg.) | % CH$_4$ in feed stream (avg.) | % CO$_2$ removed (avg.) |
|---|---|---|---|
| DI Water | 62.9 | 59.4 | ~9 |
| 1 M NaHCO$_3$ pH 9.3 | 83.0 | 59.4 | ~59 |
| 0.6 g/L CA in 1 M NaHCO$_3$ pH 9.3 | 95.7 | 59.4 | ~90 |

Example 11

Extraction of $CO_2$ from a Mixed Gas Stream in a Hollow Fiber Membrane Bioreactor Containing MEA in the Membrane Liquid The present experiment illustrates the effect of adding carbonic anhydrase to a conventional carbon dioxide absorber.

The bioreactor set-up was essentially the same as described in Example 9. Except that the gas stream contained a mixture of 28.6% $CO_2$ (20 CCM) and 71.4% $N_2$ (50 CCM) which entered the feed side of the hollow fibers. The gas chromatography method was identical to Example 9.

Membrane Liquid

The control membrane liquid used was a monoethanol amine solution (MEA) in water (1% V/V). This was compared with a membrane liquid composed of a MEA-CA aqueous solution containing 10 parts CA and 1 part MEA and 89 parts water, corresponding to a final CA concentration of 0.3 g pure enzyme protein/L of the solution.

Results

The data are presented in Table 7. In summary a HFB with 1% MEA solution could remove 48.6% of the total $CO_2$ in the feed gas. Addition of 0.3 g/L carbonic anhydrase significantly increased $CO_2$ removal in a 1% MEA solution to 84.3%.

This shows that the carbonic anhydrase of SEQ ID NO: 14 is active in presence of MEA and can significantly improve the absorption of $CO_2$ in an MEA-containing liquid. Surprisingly, only a low amount of MEA is needed in the solution to achieve a high level of $CO_2$ removal when CA is present, compared to what is known in the art. Typical aqueous amine-based $CO_2$ absorber solutions contain in the range 15-30% amine.

TABLE 7

Effect of membrane liquid on the $CO_2$ concentration of the gas stream exiting the hollow fiber membrane bioreactor

| Flue gas mix | | Membrane liquid | | % $CO_2$ in | % $CO_2$ |
|---|---|---|---|---|---|
| % $CO_2$ | % $N_2$ | Content (V/V) | pH | Scrubbed gas | removed |
| 28.6 | 71.4 | MEA 1% | 11.25 | 14.7 | 48.6 |
| 28.6 | 71.4 | 0.3 g/L CA in 1% MEA | 10.7 | 4.5 | 84.3 |

The invention claimed is:

1. A method of using a heat stable alpha-class carbonic anhydrase for extraction of carbon dioxide from a carbon dioxide-containing medium comprising contacting a carbon dioxide-containing medium with an alpha-carbonic anhydrase, wherein the alpha-carbonic anhydrase is at least 85% identical to the carbonic anhydrase of SEQ ID NO: 14, wherein the extraction of carbon dioxide is performed at a temperature of 45° C. to 100° C., and wherein the alpha-carbonic anhydrase is heat stable and retains at least 80% carbonic anhydrase activity after incubation at 60° C. for 15 min.

2. The method of claim 1, where the alpha-class carbonic anhydrase is an isolated polypeptide selected from the group consisting of:

(a) a polypeptide having an amino acid sequence which has at least 94% identity with the amino acid sequence of SEQ ID NO: 2 or SEQ ID NO: 4, or at least 91% identity with the amino acid sequence of SEQ ID NO: 6, or at least 96% identity with the amino acid sequence of SEQ ID NO: 8, or at least 89% identity with the amino acid sequence of SEQ ID NO: 10, or at least 97% identity with the amino acid sequence of SEQ ID NO: 12;

(b) a polypeptide encoded by a nucleic acid sequence which hybridizes under high stringency conditions with the complement of a polynucleotide sequence selected from the group consisting of SEQ ID NO: 1, SEQ ID NO:3, SEQ ID NO: 5, SEQ ID NO: 7, SEQ ID NO: 9 and SEQ ID NO: 11, wherein said high stringency conditions are hybridization at 42° C. in 5×SSPE, 0.3% SDS, 200 micro-g/ml sheared and denatured salmon sperm DNA, and 50% formamide, and washing three times for 15 minutes using 2×SSC in 0.2% SDS at 65° C.; and (c) a fragment of (a) or (b) having carbonic anhydrase activity.

3. The method of claim 1, wherein the alpha-class carbonic anhydrase is an isolated polypeptide having an amino acid sequence which has at least 97% identity to the amino acid sequence of SEQ ID NO: 2, SEQ ID NO: 4, SEQ ID NO: 6, SEQ ID NO: 8, SEQ ID NO: 10, or SEQ ID NO: 12, or a functional fragment thereof having carbonic anhydrase activity.

4. The method of claim 1, where the heat-stable carbonic anhydrase is used in a bioreactor.

5. The method of claim 4, wherein the bioreactor comprises a contained liquid membrane (CLM).

6. The method of claim 4, wherein the liquid membrane is a bicarbonate buffer with a pH of at least 9.0.

7. The method of claim 1, wherein the carbon dioxide-containing medium is a gas.

8. The method of claim 7, where the carbonic dioxide-containing gas is emitted from combustion or fermentation.

9. The method of claim 8, where the gas is a flue gas.

10. The method of claim 7, where the carbonic dioxide-containing gas is a raw natural gas or a syngas.

11. The method of claim 7, where the carbonic dioxide-containing gas is a biogas.

12. The method of claim 1, where the carbon dioxide-containing medium is a liquid.

13. The method of claim 1, wherein the carbon dioxide-containing medium is a multiphase mixture.

14. The method of claim 1, wherein the extraction of carbon dioxide is performed at temperatures between 45° C. and 60° C.

15. The method of claim 1, wherein the extraction of carbon dioxide is performed at a temperature of 45° C. to 80° C.

16. The method of claim 1, wherein the extraction of carbon dioxide is performed at a temperature of 45° C. to 55° C.

17. The method of claim 1, wherein the alpha-carbonic anhydrase has at least 99% sequence identity to the carbonic anhydrase of SEQ ID NO: 14 or enzymatically active fragment thereof.

18. The method of claim 1, wherein the alpha-carbonic anhydrase comprises the carbonic anhydrase of SEQ ID NO: 14.

19. The method of claim 1, wherein the alpha-carbonic anhydrase consists of the carbonic anhydrase of SEQ ID NO: 14.

20. A method of using a heat stable alpha-class carbonic anhydrase for extraction of carbon dioxide from a carbon dioxide-containing medium comprising contacting a carbon dioxide-containing medium with an alpha-carbonic anhydrase, wherein the alpha-carbonic anhydrase is at least 95% identical to the carbonic anhydrase of SEQ ID NO: 14, wherein the extraction of carbon dioxide is performed at a temperature of 45° C. to 100° C., and wherein the alpha-carbonic anhydrase is heat stable and retains at least 80% carbonic anhydrase activity after incubation at 60° C. for 15 min.

21. The method of claim 20, wherein the extraction of carbon dioxide is performed at a temperature of 45° C. to 80° C.

22. The method of claim 20, wherein the extraction of carbon dioxide is performed at a temperature of 45° C. to 60° C.

23. The method of claim 20, wherein the extraction of carbon dioxide is performed at a temperature of 45° C. to 55° C.

24. A method of using a heat stable alpha-class carbonic anhydrase for extraction of carbon dioxide from a carbon dioxide-containing medium comprising contacting a carbon dioxide-containing medium with an alpha-carbonic anhydrase, wherein the alpha-carbonic anhydrase is at least 99% identical to the carbonic anhydrase of SEQ ID NO: 14, wherein the extraction of carbon dioxide is performed at a temperature of 45° C. to 100° C., and wherein the alpha-carbonic anhydrase is heat stable and retains at least 80% carbonic anhydrase activity after incubation at 60° C. for 15 min.

25. The method of claim 24, wherein the extraction of carbon dioxide is performed at a temperature of 45° C. to 80° C.

26. The method of claim 24, wherein the extraction of carbon dioxide is performed at a temperature of 45° C. to 60° C.

27. The method of claim 24, wherein the extraction of carbon dioxide is performed at a temperature of 45° C. to 55° C.

28. A bioreactor for extracting carbon dioxide, where said reactor comprises a bicarbonate buffer with a pH of at least 9.0 and a heat stable carbonic anhydrase which is at least 85% identical to the carbonic anhydrase of SEQ ID NO: 14, wherein the heat stable carbonic anhydrase retains at least 80% carbonic anhydrase activity after incubation at 60° C. for 15 min.

29. The bioreactor of claim 28, wherein the alpha-carbonic anhydrase has at least 90% sequence identity to SEQ ID NO: 14 or enzymatically active fragment thereof.

30. The bioreactor of claim 28, wherein the alpha-carbonic anhydrase has at least 95% sequence identity to SEQ ID NO: 14 or enzymatically active fragment thereof.

31. The bioreactor of claim 28, wherein the alpha-carbonic anhydrase comprises the carbonic anhydrase of SEQ ID NO: 14.

32. The bioreactor of claim 28, wherein the alpha-carbonic anhydrase consists of the carbonic anhydrase of SEQ ID NO: 14.

* * * * *